United States Patent
Lavon

(10) Patent No.: US 8,299,237 B2
(45) Date of Patent: Oct. 30, 2012

(54) NUCLEIC ACID SEQUENCES COMPRISING NF-κB BINDING SITE WITHIN O(6)-METHYLGUANINE-DNA-METHYLTRANSFERASE (MGMT) PROMOTER REGION AND USES THEREOF FOR THE TREATMENT OF CANCER AND IMMUNE-RELATED DISORDERS

(75) Inventor: Iris Lavon, Kfar Saba (IL)

(73) Assignee: Hadasit Medical Research Services & Development Ltd., Jerusalem (IL)

(*) Notice: Subject to any disclaimer, the term of this patent is extended or adjusted under 35 U.S.C. 154(b) by 0 days.

(21) Appl. No.: 12/674,536

(22) PCT Filed: Aug. 28, 2008

(86) PCT No.: PCT/IL2008/001169
§ 371 (c)(1),
(2), (4) Date: Apr. 29, 2010

(87) PCT Pub. No.: WO2009/027978
PCT Pub. Date: Mar. 5, 2009

(65) Prior Publication Data
US 2010/0317722 A1    Dec. 16, 2010

Related U.S. Application Data

(60) Provisional application No. 60/969,057, filed on Aug. 30, 2007, provisional application No. 60/969,225, filed on Aug. 31, 2007.

(51) Int. Cl.
*C07H 21/04* (2006.01)

(52) U.S. Cl. .................. 536/24.5; 536/24.31; 536/24.1; 435/6; 435/325; 435/375

(58) Field of Classification Search .................. None
See application file for complete search history.

(56) References Cited

U.S. PATENT DOCUMENTS

| 6,022,863 A * | 2/2000 | Peyman ..................... 514/44 R |
| 7,341,835 B2 * | 3/2008 | Blume et al. .................. 435/6.1 |
| 2004/0097446 A1 | 5/2004 | Gaarde | |

FOREIGN PATENT DOCUMENTS

| CN | 1580278 | 2/2005 |
| WO | 99/14226 | 3/1999 |
| WO | 00/56746 | 9/2000 |
| WO | 00/56748 | 9/2000 |
| WO | 01/25248 | 4/2001 |
| WO | 02/28875 | 4/2002 |
| WO | 02/077272 | 10/2002 |
| WO | 03/006475 | 1/2003 |
| WO | 03/044226 | 5/2003 |
| WO | 03/051901 | 6/2003 |
| WO | 03/052132 | 6/2003 |
| WO | 03/052133 | 6/2003 |
| WO | 03/052134 | 6/2003 |
| WO | 03/095467 | 11/2003 |
| WO | 2004/035803 | 4/2004 |
| WO | 2004/101816 | 11/2004 |
| WO | 2007/016668 | 2/2007 |

OTHER PUBLICATIONS

Amit S. and Ben Neriah Y., (2003) NF-kappaB activation in cancer: a challenge for ubiquitination- and proteasome-based therapeutic approach. Semin. Cancer Biol. 13(1):15-28.
Baldwin AS., (2001) Control of oncogenesis and cancer therapy resistance by the transcription factor NF-kappaB. J. Clin. Invest. 107(3):241-6.
Biswas T. et al., (1999) Activation of human O6-methylguanine-DNA methyltransferase gene by glucocorticoid hormone. Oncogene 18(2):525-32.
Boldogh I. et al., (1998) Regulation of expression of the DNA repair gene O6-methylguanine-DNA methyltransferase via protein kinase C-mediated signaling. Cancer Res. 58(7):3950-6.
Bredel M. et al., (2006) Tumor necrosis factor-alpha-induced protein 3 as a putative regulator of nuclear factor-kappaB-mediated resistance to O6-alkylating agents in human glioblastomas. J. Clin. Oncol. 24(2):274-87.
Brell M. et al., (2005) Prognostic significance of O6-methylguanine-DNA methyltransferase determined by promoter hypermethylation and immunohistochemical expression in anaplastic gliomas. Clin. Cancer Res. 11(14):5167-74.
Citron M. et al., (1991) O6-methylguanine-DNA methyltransferase in human normal and tumor tissue from brain, lung, and ovary. Cancer Res. 51(16):4131-4.
Esteller M. et al., (2000) Inactivation of the DNA-repair gene MGMT and the clinical response of gliomas to alkylating agents. N. Engl. J. Med. 343(19):1350-4.
Ghosh S. et al., (1998) NF-kappa B and Rel proteins: evolutionarily conserved mediators of immune responses. Annual Review of Immunology 16:225-60. Harris LC. et al., (1991) Characterization of the promoter region of the human O6-methylguanine-DNA methyltransferase gene. Nucleic Acids Res. 19(22):6163-7.
Hegi ME. et al., (2005) MGMT gene silencing and benefit from temozolomide in glioblastoma. N. Engl. J. Med. 352 (10):997-1003.
Hermisson M. et al., (2006) O6-methylguanine DNA methyltransferase and p53 status predict temozolomide sensitivity in human malignant glioma cells. J. Neurochem. 96(3):766-76.
Karin Michael et al., (2004) The IKK NF-kappa B system: a treasure trove for drug development. Nature Rev 3 (1):17-26.
Kokkinakis Demetrius M, (2006) Methionine-stress: a pleiotropic approach in enhancing the efficacy of chemotherapy. Cancer Letters 233(2):195-207.

(Continued)

*Primary Examiner* — Kimberly Chong
(74) *Attorney, Agent, or Firm* — Roach Brown McCarthy & Gruber, P.C.; Kevin D. McCarthy

(57) ABSTRACT

The invention relates to nucleic acid sequences comprising NF-κB binding sites derived from the MGMT promoter region and uses thereof as decoy molecules in the treatment of cancer and immune-related disorders. More particularly, the invention relates to nucleic acid sequences as well as to modified oligonucleotides (ODNs) comprising NF-κB binding sites derived from the MGMT promoter region, and uses thereof as decoy molecules for inhibiting NF-κB enhanced expression of MGMT. The invention further relates to compositions, kits and screening methods using the NF-κB binding sites of the invention or ODNs comprising the same for treating cancer and immune related disorders.

19 Claims, 13 Drawing Sheets

OTHER PUBLICATIONS

Figure 1C:
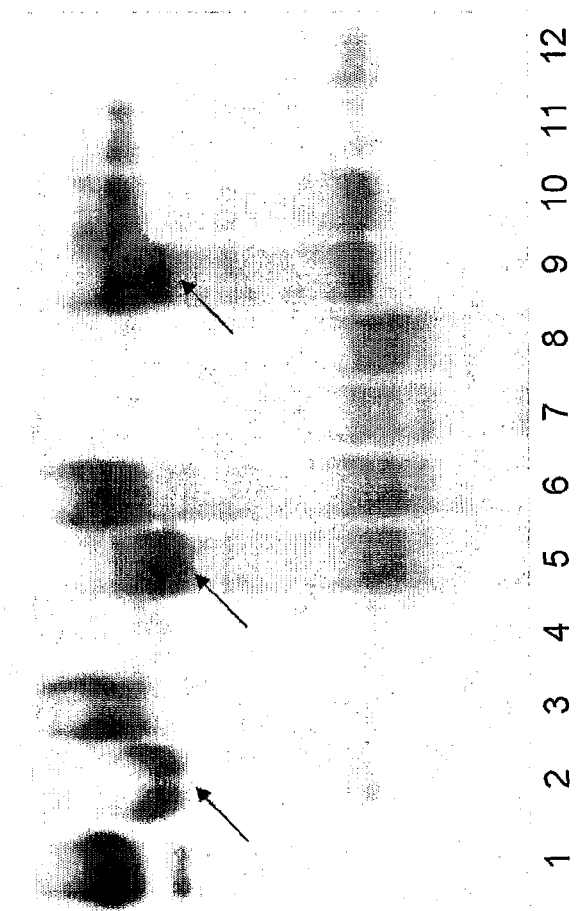

Lavon Iris et al., (2007) Novel mechanism whereby nuclear factor kappaB mediates DNA damage repair through regulation of O(6)-methylguanine-DNA-methyltransferase. Cancer research 67(18):8952-9.

Lin Z. et al., (2005) The hypermethylation and protein expression of p16 INK4A and DNA repair gene O6-methylguanine-DNA methyltransferase in various uterine cervical lesions. J. Cancer Res. Clin. Oncol. 131(6):364-70.

Margison GP. et al., (2003) Variability and regulation of O6-alkylguanine-DNA alkyltransferase. Carcinogenesis 24 (4):625-35.

Nakatsu Yoshimichi et al., (1993) Organization and expression of the human gene for O6-methylguanine-DNA methyltransferase. Mutation Research 293(2):119-32.

Patel SA. et al., (1997) Aberrant silencing of the CpG island-containing human O6-methylguanine DNA methyltransferase gene is associated with the loss of nucleosome-like positioning. Mol Cell Biol 17(10):5813-22.

Pollack IF. et al., (2006) O6-methylguanine-DNA methyltransferase expression strongly correlates with outcome in childhood malignant gliomas: results from the CCG-945 Cohort. J. Clin. Oncol. 24(21):3431-7.

Senftleben U. and Karin M., (2002) The IKK/NF-kappaB pathway. Crit. Care Med. 30(1 supp):S18-S26.

Shi N., (2001) Receptor-mediated gene targeting to tissues in vivo following intravenous administration of pegylated immunoliposomes. Pharm Res. 18(8):1091-5.

Silber Jr. et al., (1996) Lack of the DNA repair protein O6-methylguanine-DNA methyltransferase in histologically normal brain adjacent to primary human brain tumors. Proc. Natl. Acad. Sci. U S A 93(14):6941-6.

Son HJ. and Kim JS., (2007) Therapeutic efficacy of DNA-loaded PLGA microspheres in tumor-bearing mice. Arch Pharm. Res. 30(8):1047-50.

Srivenugopal KS., (1996) Ubiquitination-dependent proteolysis of O6-methylguanine-DNA methyltransferase in human and murine tumor cells following inactivation with O6-benzylguanine or 1,3-bis(2-chloroethyl)-1-nitrosourea. Biochemistry 35(4):1328-34.

Takashima Y., (2007) Spray-drying preparation of microparticles containing cationic PLGA nanospheres as gene carriers for avoiding aggregation of nanospheres. Int. J. Pharm. 343(1-2):262-9.

Washington WJ. et al., (1989) Age-dependent modulation of tissue-specific repair activity for 3-methyladenine and O6-methylguanine in DNA in inbred mice. Mech. Ageing Dev. 48(1):43-52.

Watts GS. et al., (1997) Methylation of discrete regions of the O6-methylguanine DNA methyltransferase (MGMT) CpG island is associated with heterochromatinization of the MGMT transcription start site and silencing of the gene. Mol Cell Biol 17(9):5612-9.

Weaver KD. et al., (2003) Potentiation of chemotherapeutic agents following antagonism of nuclear factor kappa B in human gliomas. J. Neurooncol. 61(3):187-96.

Wu ZH. et al., (2006) Molecular linkage between the kinase ATM and NF-kappaB signaling in response to genotoxic stimuli. Science 311(5764):1141-6.

Database EMBL [Online] Nov. 25, 1991, *Homo sapiens* DNA for O6-methylguanine-DNA-methyltransferase promoter. XP002505259 retrieved from EBI accession No. EMBL:X61657.

\* cited by examiner

-954    (-766) TCTGTAAAGTCCCC (-752)    (-90) GCGGGAACACCCCGC (-75)    +1

MGMT-κB 1      MGMT-κB 2

Fig. 1A

Consensus HIVkB GGCTTCAGAGGGGACTTTCCGAGA
MGMT-kB 1 [(-773) – (-734)] TGATGGCTTCTGTAAAGTCCCCATCTCCAAATAAGGTCAC
MGMT-kB 2 [(-91) – (-68)] GGCGGGAACACCCCGCCCCCG MGMT-kB 1 Mut TGATGGCTTCTGTAAAGTCGGCATCTCCAAATAAGGTCAC
MGMT-kB 2 Mut GGCGGGAACACGGGCGCCCCG
SP1 CTAACTCCGCCCATCT

Fig. 1B

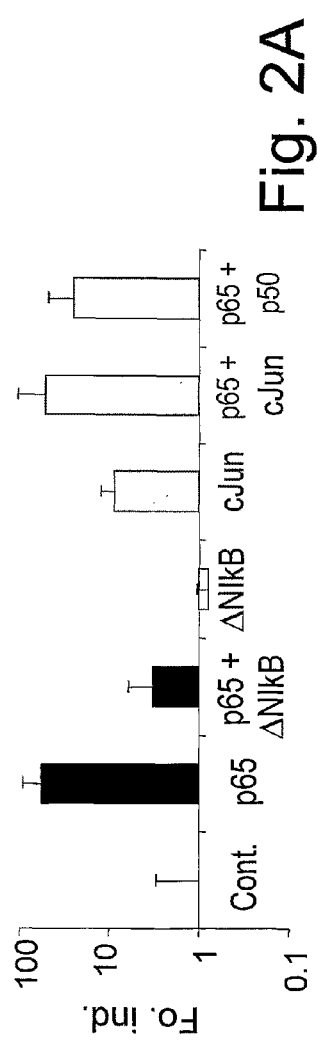
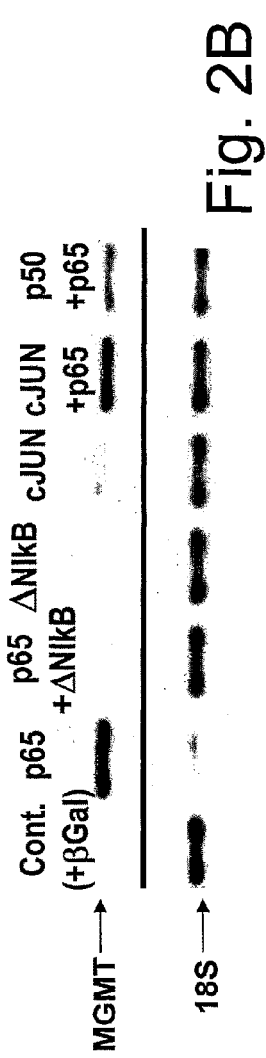
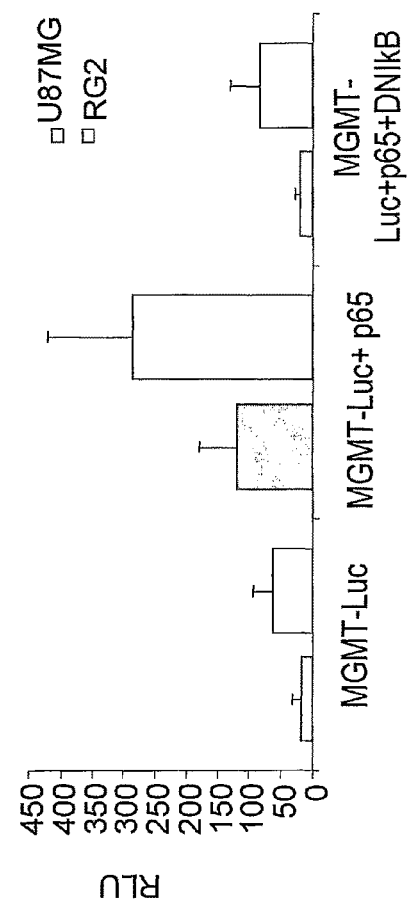
Fig. 2A
Fig. 2B
Fig. 2C

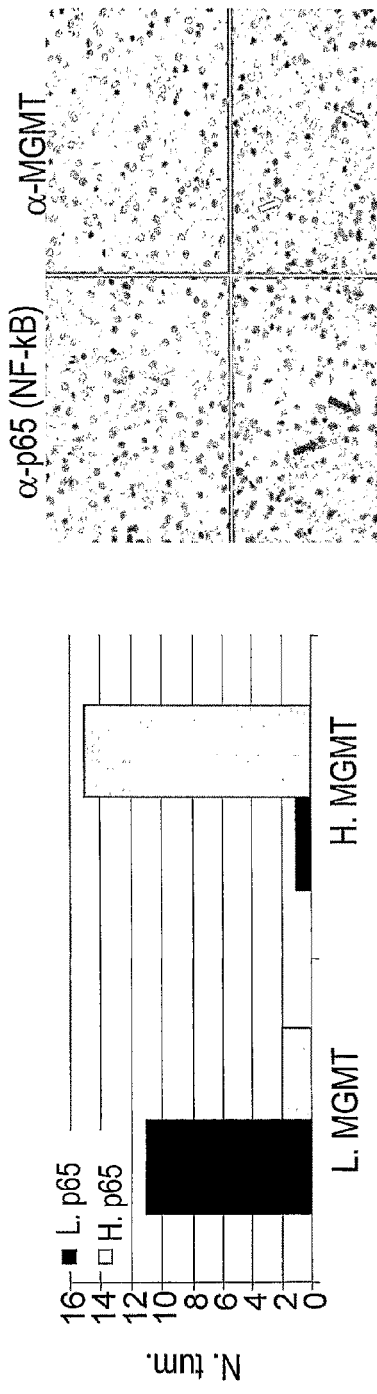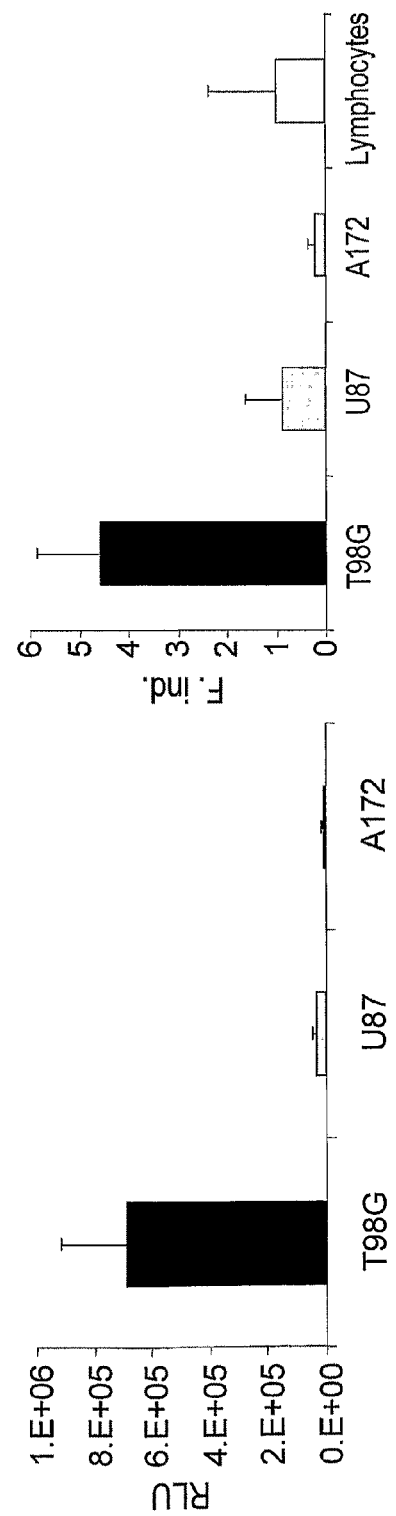
Fig. 3A
Fig. 3B
Fig. 3C
Fig. 3D

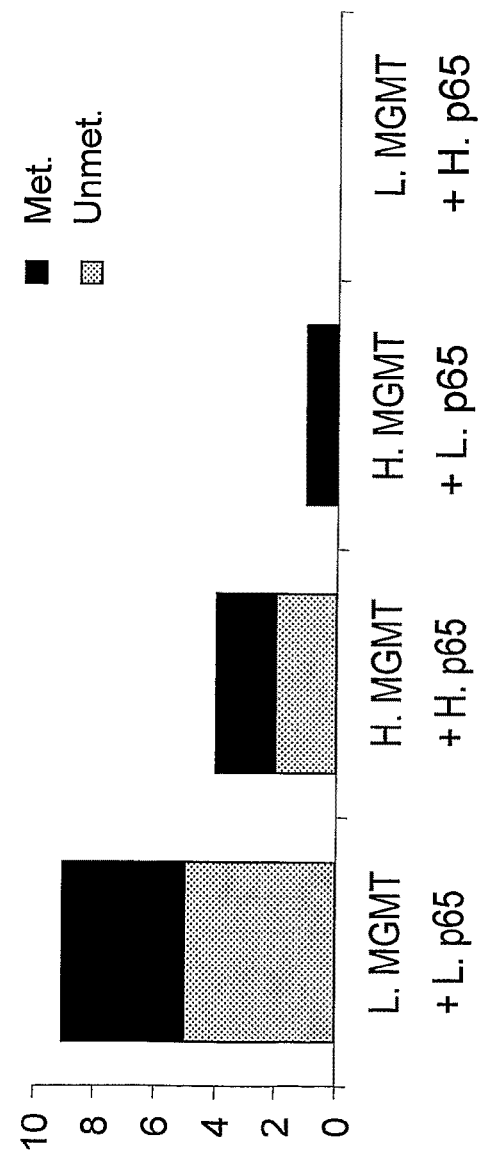

```
                    K3
-894 agggaaggt ctgtcctctt aggcttctgg tggcttgcag gtgcagccct ccaatcctcc -834 tccccaagcg gcctgctgcc tataaggaca cgagtcatac tggatgaggg gcccactaat
                     K1
-774 tgatggcttc tgtaaagtcc ccatctccaa ataaggtcac attgtgaggt actgggagtt -714 aggactccaa catagcttct ctggtggaca caattcaact cctaataacg tccacacaac -654 cccaagcagg gcctggcacc ctgtgtgctc tctggagagc ggctgagtca ggctctggca -594 gtgtctaggc catcggtgac tgcagcccct ggacggcatc gcccaccaca ggccctggag -534 gctgccccca cggccccctg acagggtctc tgctggtctg ggggtccctg actaggggag -474 cggccccagg aggggagaga ctcgcgctcc gggctcagcg tagccgcccc gagcaggacc -414 gggattctca ctaagcgggc gccgtcctac gaccccccgcg cgctttcagg accactcggg
                                 K4
-354 cacgtggcag gtcgcttgca cgcccgcgga ctatccctgt gacaggaaaa ggtacgggcc -294 atttggcaaa ctaaggcaca gagcctcagg cggaagctgg gaaggcgccg cccggcttgt -234 accggccgaa gggccatccg ggtcaggcgc acagggcagc ggcgctgccg gaggaccagg -174 gccggcgtgc cggcgtccag cgaggatgcg cagactgcct caggcccggc gccgccgcac
                                     K2
-114 tgggcatgcg ccgacccggt cgggcgggaa caccccgccc cgcccgggct ccgcccagc
                                                             ↓
-54  tccgccccg cgcgccccgg ccccgccccc gcgcgctctc ttgcttttct caggtcctcg 7  gctccgcccc gctctagacc ccgccccacg ccgccatccc cgtgccccctc ggccccgccc
                       K5
 67  ccgcgccccg gatatgctgg gacagcccgc
```

Fig. 11

NUCLEIC ACID SEQUENCES COMPRISING NF-κB BINDING SITE WITHIN O(6)-METHYLGUANINE-DNA-METHYLTRANSFERASE (MGMT) PROMOTER REGION AND USES THEREOF FOR THE TREATMENT OF CANCER AND IMMUNE-RELATED DISORDERS

REFERENCE TO CO-PENDING APPLICATIONS

Priority is claimed as a 371 of international of PCT/IL2008/001169, filed on Aug. 28, 2008, which claims priority to U.S. provisional patent application Nos. 60/969,057, filed on Aug. 30, 2007 and 60/969,225, filed on Aug. 31, 2007.

FIELD OF THE INVENTION

The invention relates to nucleic acid sequences derived from the MGMT promoter region and uses thereof in the treatment of cancer and immune-related disorders. More particularly, the invention relates to nucleic acid sequences as well as to modified oligonucleotides (ODNs) comprising NF-κB binding sites derived from the MGMT promoter region, as well as to compositions, kits and methods thereof for treating cancer and immune related disorders.

BACKGROUND OF THE INVENTION

All publications mentioned throughout this application are fully incorporated herein by reference, including all references cited therein.

NF-κB is a family of dimeric transcription factors. The inhibitor of κB (I-κB) retains NE-κB in the cytoplasm and following exposure to extracellular inducers it undergoes phosphorylation, ubiquination and subsequent degradation. This in turn, allows NF-κB to translocate into the nucleus, where it bind a common sequence motif known as the NF-κB site [Ghosh, S. et al. Annual Review of Immunology 16:225-60 (1998)] and stimulates gene expression (for review, see [Senftleben, U. and Karin, M. Crit. Care Med. 30:S18-S26 (2002)].

DNA damage induced by the alkylating agent 1,3-bis(2-chloroethyl)-1-nitrosourea (BCNU) results in a marked increase in NF-κB activity [Weaver K D. et al. J. Neurooncol. 61:187-96 (2003)]. Inhibition of NF-κB activity by a super-repressor strongly enhances the apoptotic potential of the alkylating agent. Therefore, it was suggested that in human tumors the role of NF-κB in anti-apoptotic mechanisms contributes to the high incidence of chemoresistance to alkylating agents [Weaver (2003) ibid.].

Alkylating agents are highly reactive mutagens and carcinogens and their analogous compounds are used to treat human malignancies. They represent a large class of DNA damaging compounds that include drugs like temozolomide, streptozotocin, procarbazine, 1,3-bis(2-chloroethyl)-1-nitrosourea (BCNU) and dacarbazine. The lethal and mutagenic effects of these compounds is inhibited by the cellular DNA-repair enzyme O(6)-Methylguanine-DNA-Methyltransferase (MGMT), which transfers the alkyl/methyl adducts from the (O)6 atom of DNA guanine to its own cysteine residues. The guanine is then restored and the MGMT molecule is irreversibly inactivated [Srivenugopal, K S. Biochemistry 35:1328-34 (1996)]. Hence, the repair capability of MGMT is dependent on de novo protein synthesis. MGMT expression varies widely in tumor cells [Citron, M. et al. Cancer Res. 51:4131-4 (1991); Washington, W J. et al. Mech. Ageing Dev. 48:43-52 (1989)]. It has been suggested that hypermethylation of CpG islands within the promoter region is associated with epigenetic inactivation of the MGMT. Several studies demonstrated that tumor cells with MGMT promoter methylation are more sensitive to alkylating agents such as BCNU and temozolomide [Hegi, M E. et al. N. Engl. J. Med. 352:997-1003 (2005); Danam, R P. et al. Int. J. Oncol. 18:1187-93 (2001); Silber, J R. et al. Proc. Natl. Acad. Sci. USA 93:6941-6 (1996)].

On the other hand, over-expression of MGMT in tumors has a protective effect against cell death induced by chlorethylating and methylating agents, in both experimental and clinical settings Inhibition of MGMT activity, using an artificial substrate such as O6-Benzylguanine (BG), sensitizes the tumor cells to the toxic effects of chemotherapeutic alkylating agents [Esteller, M. et al. N. Engl. J. Med. 343:1350-4 (2000)].

These data indicate that MGMT expression is a crucial player in tumor drug resistance and is an ideal target for modulation. Therefore, an understanding of the molecular mechanisms that control MGMT expression may have major clinical implications.

The promoter region of MGMT has been cloned and sequenced [Harris, L C. et al. Nucleic Acids Res. 19:6163-7 (1991)]. The function of the transcription factors glucocorticoid-responsive element (GRE) [Biswas, T. et al. Oncogene 18:525-32 (1999)] and AP-1 [Boldogh, I. et al. Cancer Res. 58:3950-6 (1998)] in the regulation of MGMT have been described. As shown by the present invention, the inventors identified several putative NF-κB binding sites in the MGMT promoter region and analyzed their role in the regulation of MGMT expression. Using electrophoretic mobility shift assay (EMSA) the inventors found that NF-κB binds specifically to the MGMT promoter and showed that transient transfection of HEK293 cells with the NF-κB subunit p65 induced a 55-fold increase in MGMT expression. The relationships between NF-κB and MGMT were further demonstrated in glioma cell lines and human glial tumors. The inventors found a significant correlation between the extent of NF-κB activation and MGMT expression which was independent of MGMT promoter methylation. The inventors further demonstrated that ectopic expression of p65 or high constitutive NF-κB activity has a protective effect against alkylating agents. This protective effect seems to be solely dependent on MGMT. In view of the fact that a large proportion of tumor cells display high constitutive activation of NF-κB (for review, see [Amit, S. et al. Semin. Cancer Biol. 13:15-28 (2003)]), and that such tumors usually exhibit increased resistance to chemotherapy [Baldwin, A S. J. Clin. Invest. 107: 241-6 (2001)] these results are of great clinical importance.

It is therefore one object of the invention to provide a nucleic acid sequence derived from the MGMT promoter region, comprising an NF-κB binding site.

Another object of the invention is to provide a modified nucleic acid sequence comprising at least one copy of an MGMT NF-κB binding site of the invention as an NF-κB decoy. The invention further provides compositions, combinations, kits, methods and uses of said decoy molecule for treating immune related disorders. In yet another object, the invention provides the use of the decoy molecules of the invention and any composition and kits thereof for increasing cell sensitivity to therapeutic agents causing DNA damage, in a subject in need thereof.

It yet another object, the invention relates to a screening method for a compound which inhibits NF-κB mediated expression of MGMT and thereby may be used for treating immune related disorders, also by increasing sensitivity to therapeutic agents.

These and other objects of the invention will become apparent as the description proceeds.

SUMMARY OF THE INVENTION

In a first aspect, the invention relates to an isolated and purified nucleic acid sequence derived from the O(6)-Methylguanine-DNA-Methyltransferase (MGMT) promoter region. The nucleic acid sequence of the invention comprises at least one NF-κB binding site.

A second aspect of the invention relates to a construct comprising at least one repeat of a nucleic acid sequence of at least one NF-κB binding site derived from the MGMT promoter region.

A third aspect of the invention relates to an NF-κB decoy in the form of an oligonucleotide (ODN) or oligonucleotide analogue comprising at least one repeat of a nucleic acid sequence comprising at least one NF-κB binding site derived from the MGMT promoter region.

According to a further aspect, the invention relates to a composition comprising as an active ingredient an effective amount of at least one NF-κB decoy in the form of an oligonucleotide (ODN) or oligonucleotide analogue comprising at least one repeat of a nucleic acid sequence of at least one NF-κB binding site derived from the MGMT promoter region.

According to another preferred embodiment, any of the compositions of the invention may be used for inhibiting the NF-κB mediated enhancement of MGMT expression, and thereby for the treatment of immune-related disorders. It should be further noted that reduced expression of MGMT may lead to an increases in the sensitivity of cells to a therapeutic agent, causing DNA damage. According to another preferred embodiment the composition of the invention may be specifically suitable for the treatment of an immune related disorder in a subject in need thereof. The invention therefore further provides methods and uses of the decoy molecules of the invention or any compositions, combinations or kits thereof for treating immune-related disorders.

A further aspect of the invention relates to a screening method for a compound which inhibits NF-κB mediated expression of MGMT and thereby increase sensitivity to therapeutic agents, specifically agents causing DNA damage, in a subject in need thereof. According to one embodiment, the screening method of the invention comprises three main stages: (a) obtaining a candidate compound which binds a nucleic acid sequence comprising at least one NF-κB binding site derived from the MGMT promoter region, as defined by the invention, or any fragment, variant, derivative, homologue and mutant thereof; (b) selecting from the candidate compounds obtained in step (a), a compound which inhibits the expression of a reporter gene operably linked to a nucleic acid sequence comprising an NF-κB binding site derived from the MGMT promoter region, as defined by the invention; and (c) determining the effect of the compound selected in step (b), on MGMT expression, and thereby evaluating the potential of this compound on the sensitivity of cells, to a therapeutic agent, causing DNA damage.

These and other aspects of the invention will become apparent by the hand of the following figures.

BRIEF DESCRIPTION OF THE INVENTION

FIG. 1A-1C: Specific binding of NF-κB to two putative NF-κB sites within the MGMT promoter FIG. 1A. Location of the two NF-κB putative binding sites within the MGMT promoter region. The sites were designated MGMT-κB1 (also denoted by SEQ ID NO. 1) and MGMT-κB2 (also denoted by SEQ ID NO. 2) according to their position within the MGMT promoter.

FIG. 1B. Sequence of the oligonucleotides used for EMSA: The consensus NF-κB site from HIV LTR (HIV-κB, also denoted by SEQ ID NO. 3) served as control. The oligonucleotides with mutated sites were designated MGMT-κB1-Mut (also denoted by SEQ ID NO. 6) and MGMT-κB2-Mut (also denoted by SEQ ID NO. 7). The mutated nucleotides are in bold type and underlined.

FIG. 1C. EMSA analysis: Nuclear extracts from Hela cells exposed for 10 min to TNFα (200 u/ml) were incubated with $^{32}$P-labeled probes, as depicted. Incubation of consensus HIV-κB [lane 2, (also denoted by SEQ ID NO. 1)], MGMT-κB-1 [lane 5 (also denoted by SEQ ID NO. 1)] and MGMT-κB2 [lane 9 (also denoted by SEQ ID NO. 2)] resulted in the formation of complexes of a similar size (black arrow). Specific binding was not observed when extracts were incubated with MGMT-κB1 Mut [lane 8 (also denoted by SEQ ID NO. 6)] or MGMT-κB2 Mut [lane 12 (also denoted by SEQ ID NO. 7)] or when the incubation was carried out in the presence of a 100-fold excess of unlabeled HIV-κB probe (lanes 4, 7 and 11). Identification of the binding factor as NF-κB was confirmed by supershift analysis, using monoclonal antibodies against the p65 subunit (lanes 3, 6 and 10). Abbreviations: α (anti), co. (cold), Mut. (mutant).

FIG. 2A-2C: Induction of MGMT mRNA expression and MGMT promoter-dependent reporter gene by NF-κB/p65

FIG. 2A. HEK293 cells were transiently transfected with CMVβGal alone or along with various expression vectors as indicated. At 24 hrs following transfection, changes in MGMT expression were analyzed by real-time RT-PCR, using the Syber green assay. Fold-change (y axis) represents the relative expression of the MGMT mRNA vs that of the control group (cells transfected with CMVβgal) normalized to 18s rRNA expression. The results are expressed as the mean±s.d.

FIG. 2B. Parallel patterns were observed when the real time PCR end products from A were analyzed by agarose gel electrophoresis.

FIG. 2C. U87MG (gray bars) and RG2 (white bars) cell lines were transiently transfected with the reporter MGMT-Luc construct alone or with other plasmids as indicated. CMVβ-galactosidase expression vector (CMVβgal) was included in each transfection to normalize transfection efficiency. The obtained promoter activity is relative to the basic pGL3-luc, reporter plasmid lacking the promoter sequence. Abbreviations: fo. (fold), Ind. (induction), cont. (control).

FIG. 3A-3D: Correlation between NF-κB activation, MGMT mRNA and protein expression Summary of semi-quantitative immunohistochemical analysis of NFκB activation (nuclear translocation) and MGMT expression in 29 paraffin-embedded sections of high grade and low grade human gliomas.

FIG. 3A. Significantly more tumors with high MGMT expression (≧50% nuclear staining) are seen in the group of tumors with high nuclear NF-κB staining than in the group of tumors with low NF-κB staining (<50% nuclear staining).

FIG. 3B. Representative microscopy of MGMT and NF-κB nuclear staining assessed by immunohistochemistry. The upper panel represents a patient with negative staining of both NF-κB and MGMT; the lower panel represents a patient with positive staining.

FIG. 3C. NF-κB activation level determined by transfection with an NF-κB-luciferase reporter construct. Reporter activity is presented as the mean±s.d. of the relative luciferase activity (RLU), after normalization to β-galactosidase expression.

FIG. 3D. MGMT mRNA expression evaluated by real time RT-PCR. Fold-change (y axis) represents the relative expression of MGMT mRNA vs that of the control group (human lymphocytes) normalized to 18s rRNA expression. The results are expressed as the mean±s.d. Abbreviations: L (low), H (high), N. (number), turn. (tumors), α (anti), Fo. (fold), ind. (induction).

FIG. 4A-4B: MGMT promoter methylation status in glioma cell lines and oligodendroglioma tumors FIG. 4A. Methylation status of the MGMT promoter region in various cell lines, as determined by Methylation-Specific PCR Assay. PC=positive control for methylated DNA; NC=normal control (DNA from a normal blood sample) with an unmethylated MGMT. C=control without DNA. A 100-bp marker ladder was loaded to estimate molecular size, as shown on the right.

FIG. 4B. methylation status of 16 of the 29 tumors presented in FIG. 3. Of these tumors, 12 exhibited both low MGMT and low p65 nuclear staining (<50%), 4 tumors exhibited both high MGMT and high p65 nuclear staining (≧50%), 1 tumor showed high MGMT and low p65. Despite the significant correlation between NF-κB activation and MGMT expression, methylation of the MGMT promoter varied. Abbreviations: L (low), H (high), Met (methylated), Umet (unmethylated).

Figure 5B:
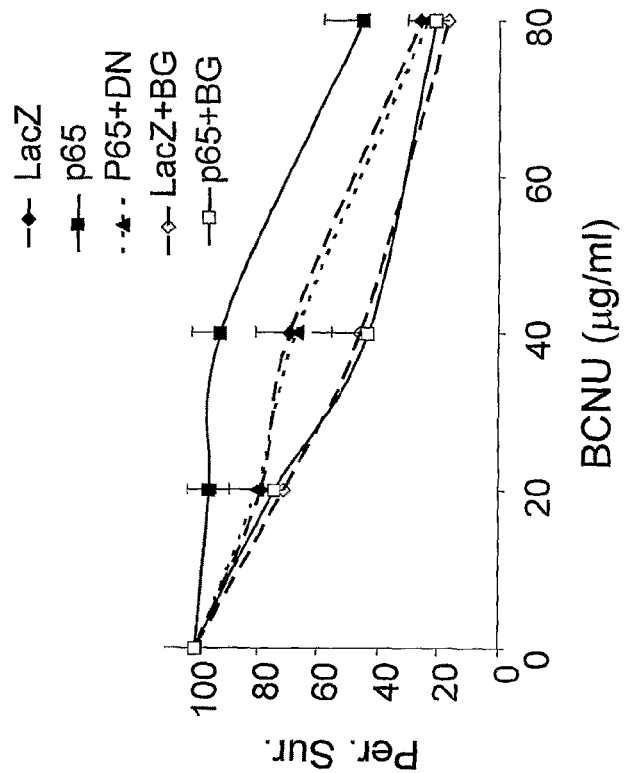
Figure 5A:
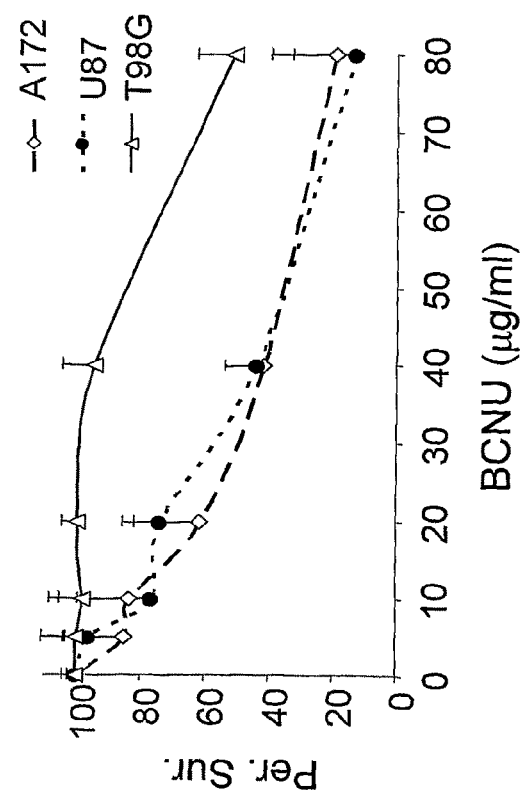

FIG. 5A-5B: NF-κB related chemoresistance to alkylating agent (BCNU).

FIG. 5A. Glioma cell lines A172, U87MG and T98G, were exposed for 2 hrs to increasing concentrations of BCNU, as indicated.

FIG. 5B. HEK293 cells transiently transfected with CMVβgal alone or along with CMVp65, or with CMVp65 and CMVΔNI-κB.

In the BG-treated groups, BG was added to the cell medium 4-6 hrs after transfection at a final concentration of 80 μM and the cells were incubated with the agent for the duration of the experiment. BCNU was added 24 hrs after transfection. A viability test was preformed 48 hrs following the BCNU treatment. Percent survival is expressed as the mean±s.d. of three different experiments. Cell line with endogenous high NF-κB activity (FIG. 5A) or with forced p65 (FIG. 5B) display lower sensitivity to nitrosourea treatment then cells with low NF-κB activity. Depletion of MGMT by BG restores chemosensitivity. Abbreviations: Per. (percent), Sur. (survival).

Figure 6:
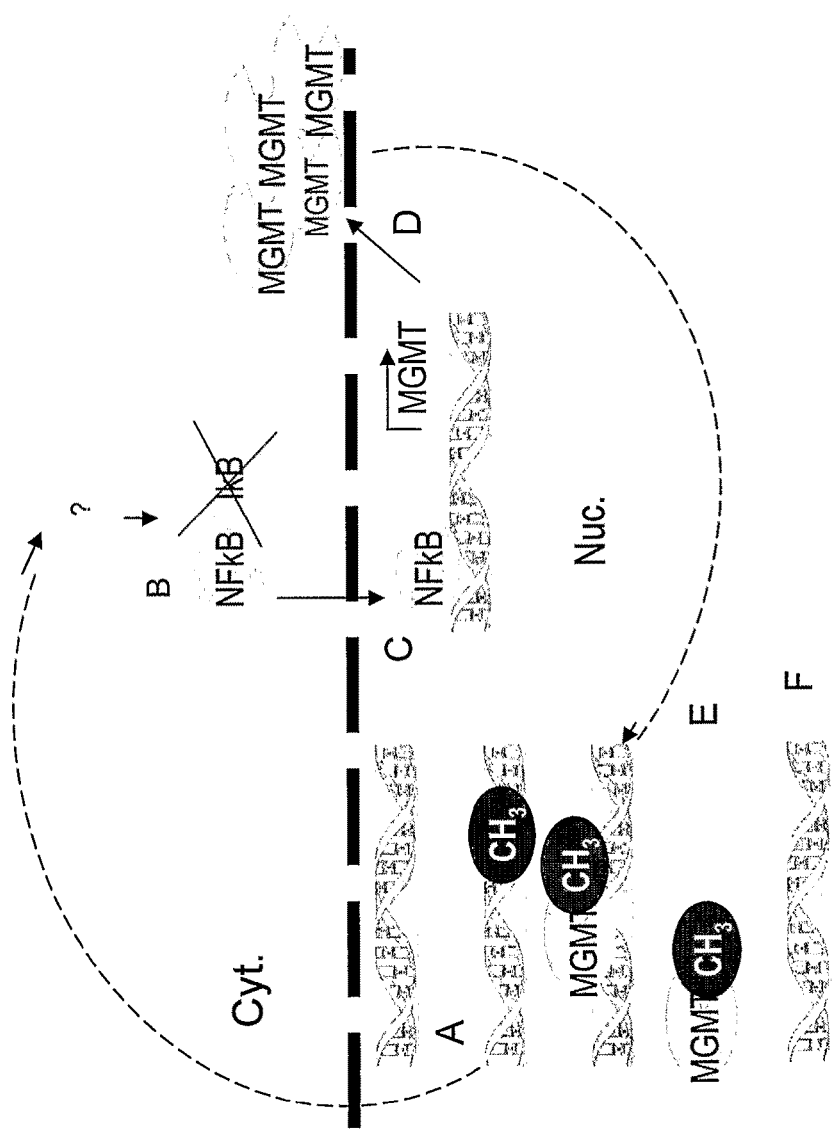

FIG. 6: A proposed simplified model for a DNA damage repair mechanism induced by NF-κB in response to alkylating agents Cell exposure to alkylating agent (A) induces NF-κB activation and subsequent degradation of I-κB (B), allowing the translocation of NF-κB into the nucleus (C), and stimulation of MGMT expression (D). MGMT removes the alkyl/methyl adducts from the (O)6 atom of DNA guanine (E) and the guanine is restored (F). Abbreviations: Cyt. (cytoplasm), Nuc. (nucleus).

Figure 7:
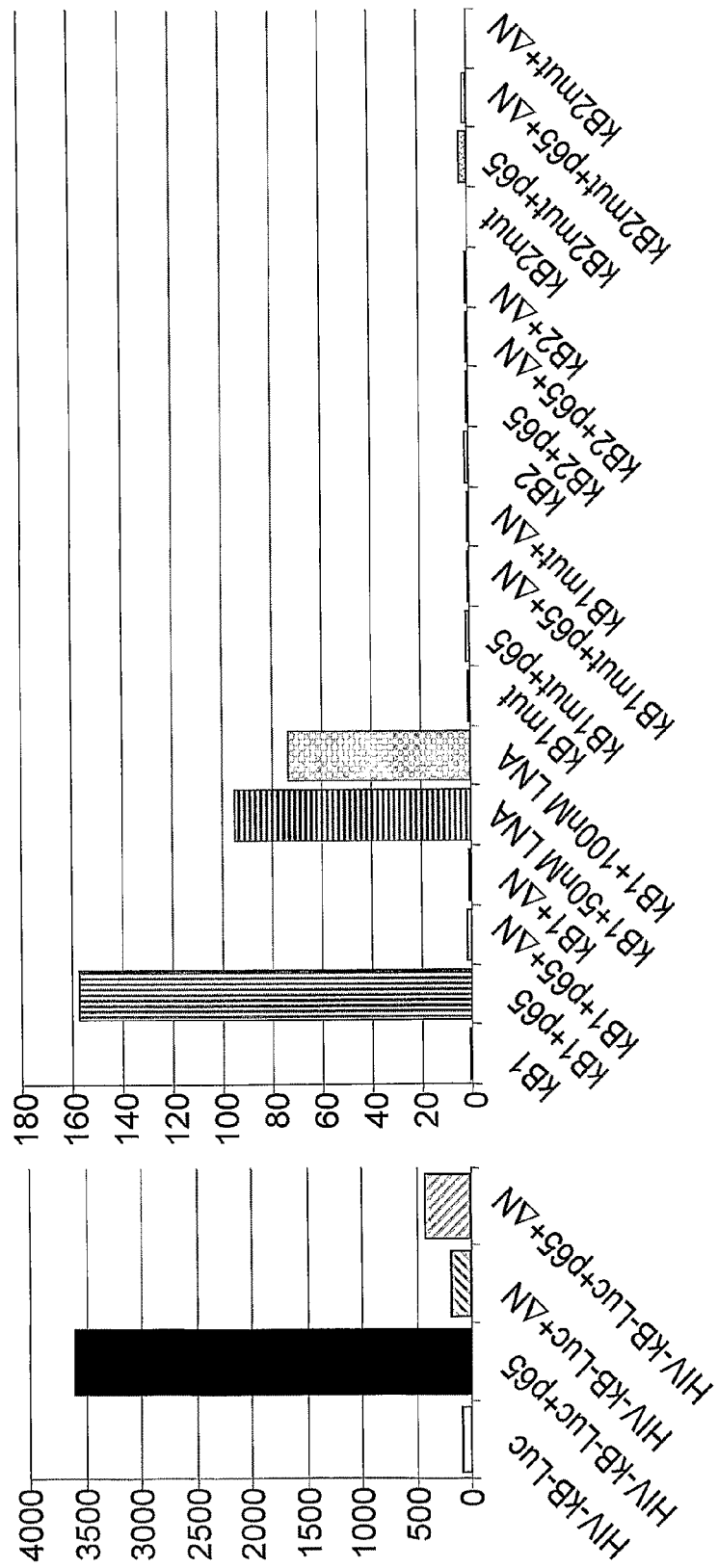

FIG. 7: Interference with NF-κB binding to MGMT-NF-κB1 site using LNA modified ODNs HEK293T cell line was transiently transfected with various reporter-gene constructs alone or with other plasmids as indicated. LNA-ODNs corresponding to the MGMT-KB1 site was added in two concentrations as indicated (also denoted by SEQ ID NO. 36 and 37). CMVβ-galactosidase expression vector (CMVβgal) was included in each transfection to normalize transfection efficiency. The obtained promoter activity is relative to the basic pGL3-luc, reporter plasmid lacking the promoter sequence. Abbreviations: Mut (mutant), Luc (luciferase).

Figure 8A:
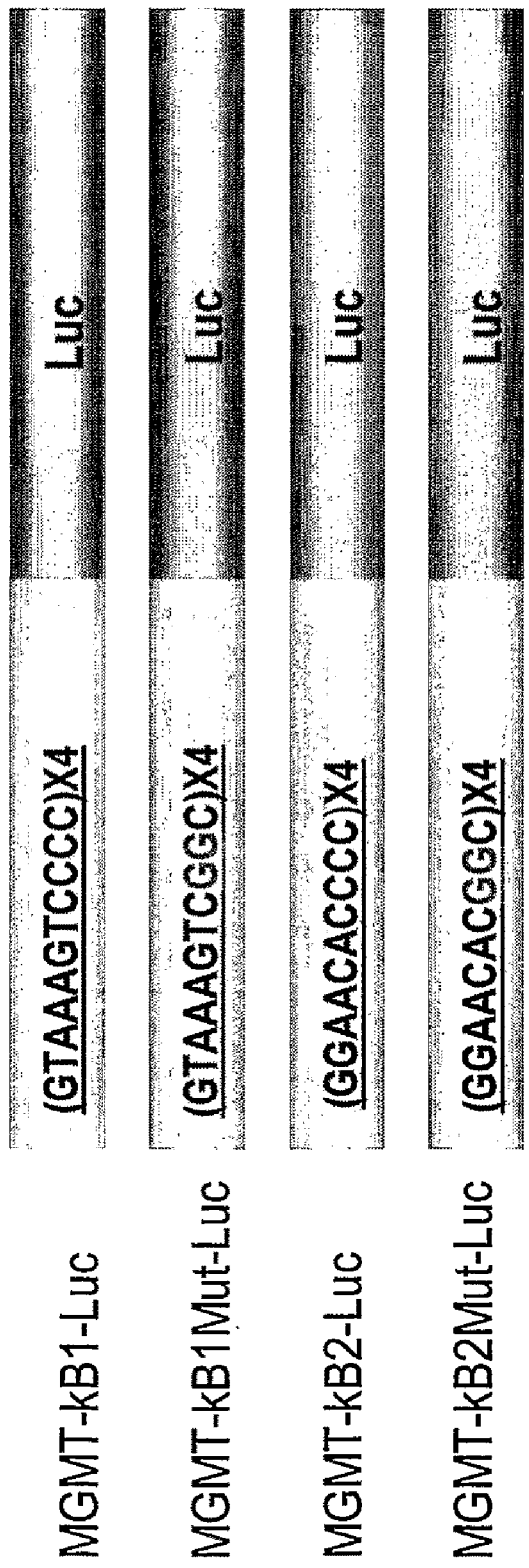
Figure 8B:
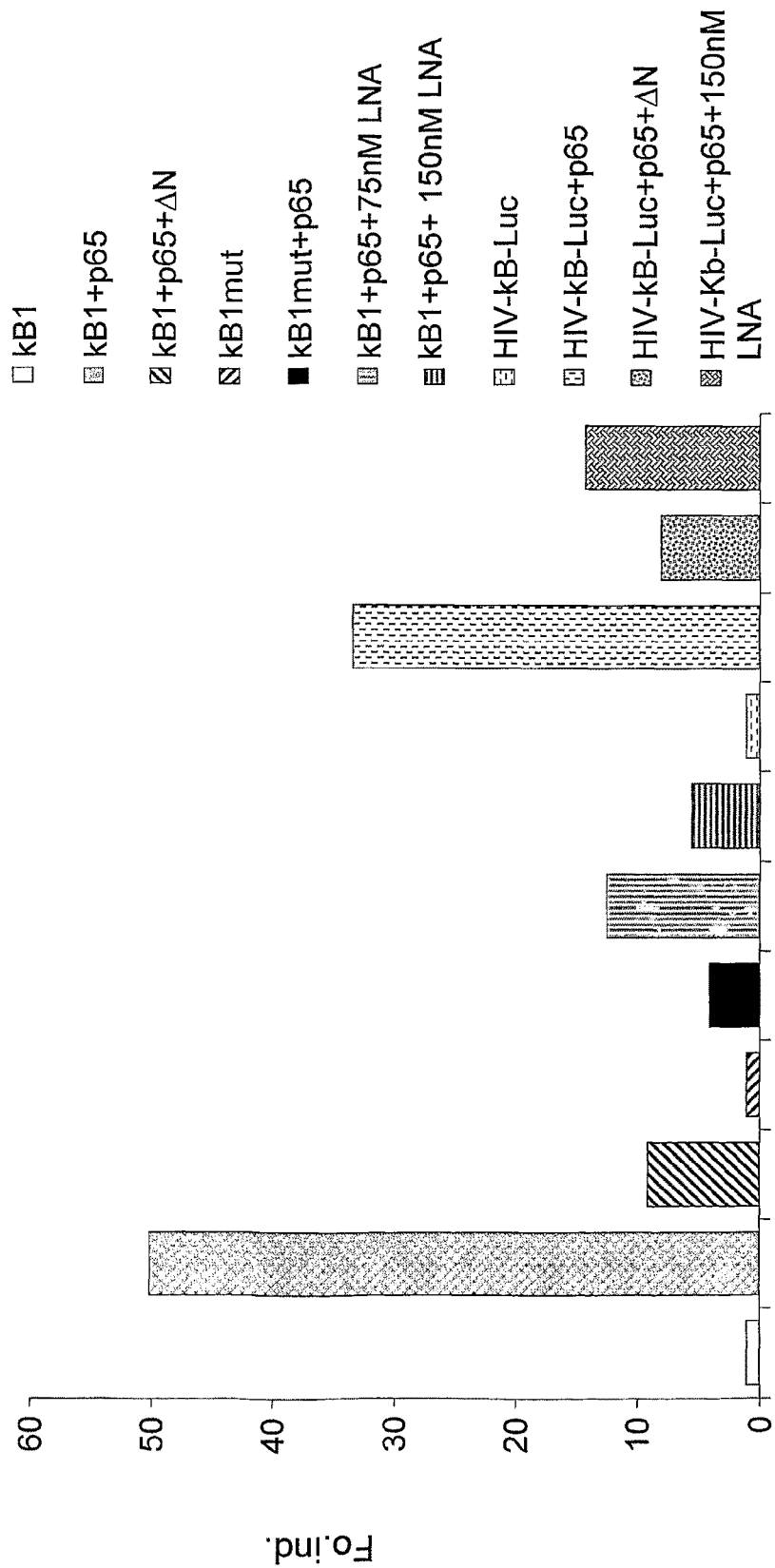

FIG. 8A-8B: MGMT-NF-κB reporter gene constructs and their induced activity and suppression FIG. 8A. luciferase reporter constructs—four copies of each of the two NF-κB sites within MGMT promoter and their corresponding mutant sites containing a C-to-G substitution were constructed and used. It should be noted that MGMT-kB1-Luc shown in the figure is also denoted by SEQ ID NO. 44, MGMT-kB1Mut-Luc is also denoted by SEQ ID NO. 45, MGMT-kB2-Luc is also denoted by SEQ ID NO. 46 and MGMT-kB2Mut-Luc is also denoted by SEQ ID NO. 47.

FIG. 8B. Interference with NF-κB binding to MGMT-NFκB1 site using modified ODN. HEK293T cell line was transiently transfected with various reporter-gene constructs alone or with other plasmids as indicated. ODN corresponding to the MGMT-kB1 site (as also denoted by SEQ ID NO. 40 and 41) was added in the indicated concentrations. CMVβ-galactosidase expression vector (CMVβgal) was included in each transfection to normalize transfection efficiency. The obtained promoter activity is relative to the corresponding reporter plasmid transfected alone. Abbreviations: Mut (mutant), Luc (luciferase). Fo. (fold), Ind. (induction).

Figure 9:
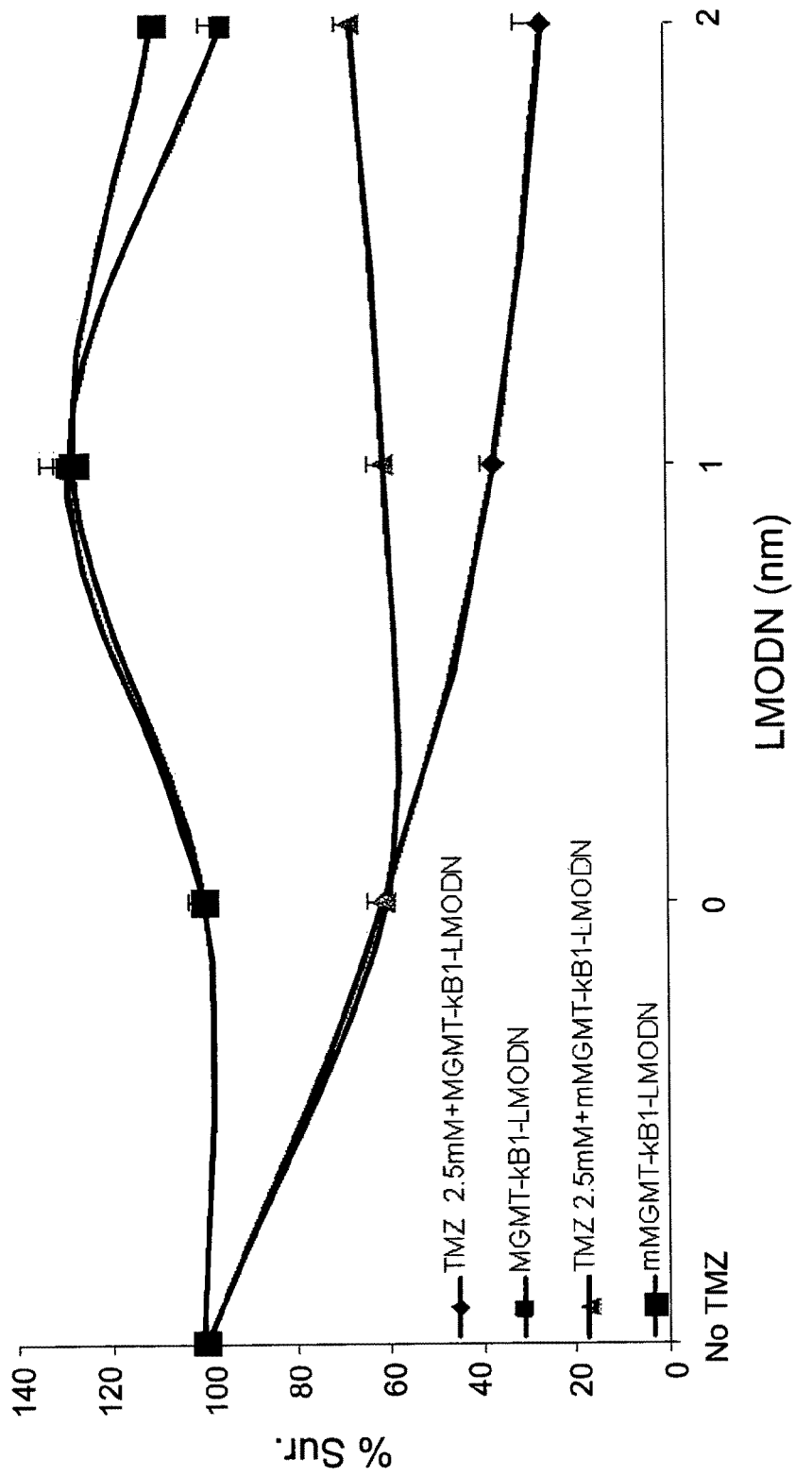

FIG. 9: The decoy ODN molecules of the invention increase sensitivity of cell lines to alkylating agents (temozolomide)

Twenty four hours following treatment with the indicated decoy ODN molecules of the invention (also denoted by SEQ ID NO. 40, 41, and the control mutant decoys of SEQ ID NO. 42 and 43), the cells are exposed for two hrs to increasing concentrations of the alkylating agent. The viability of the cells is tested 24-48 hrs later by CellTiter-Blue assay (Promega®). Cell viability estimation is done by measuring the fluorescent intensity of resorufin (ex. 560 nm, em. 590 nm) using a fluorescent microplate reader. Abbreviations: LMODN [LNA (locked nucleic acids), Modified ODN (oligonucleotide)], (mutated LMODN), TMZ (temozolomide), Sur. (survival).

Figure 10:
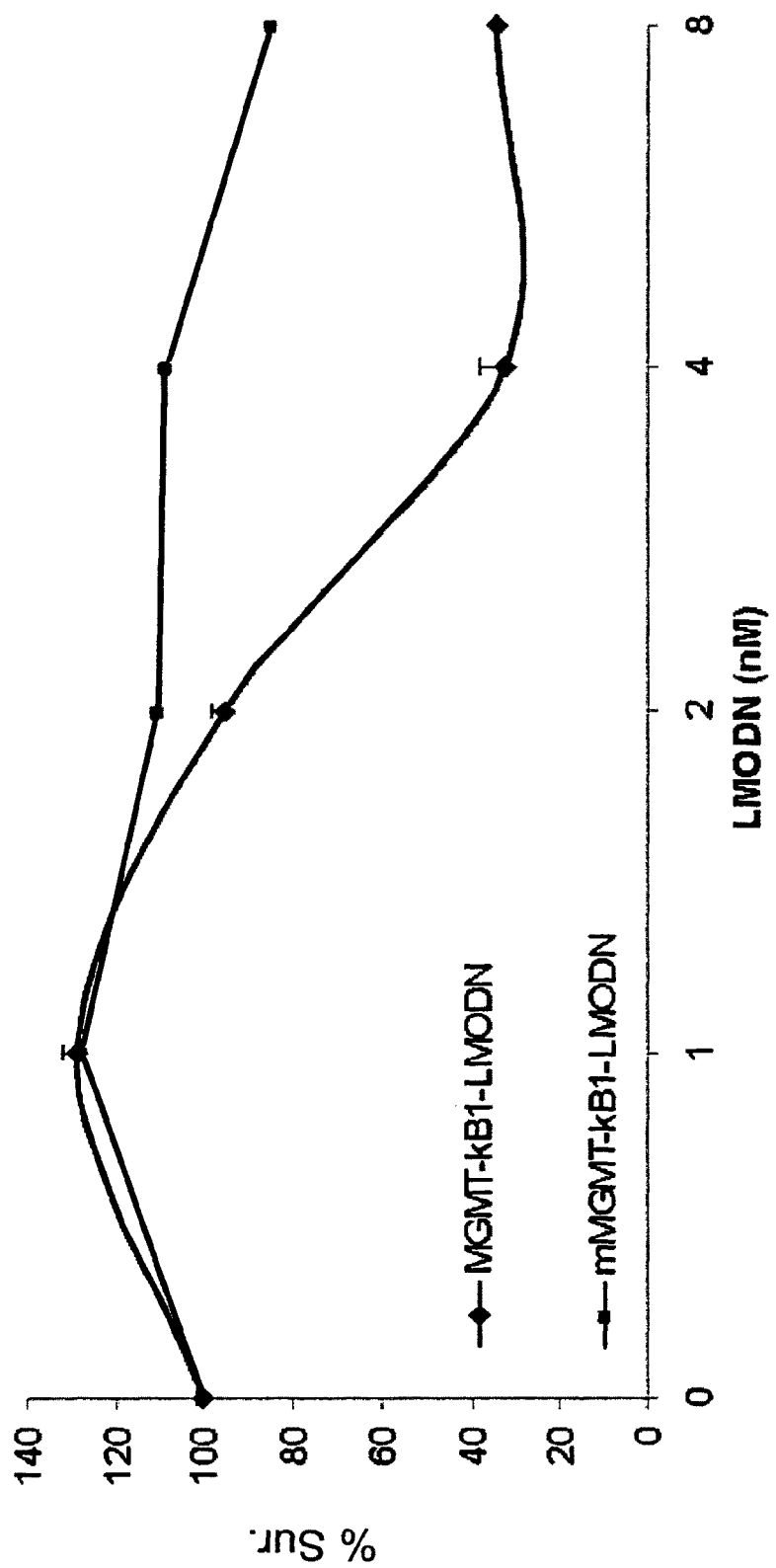

FIG. 10: MGMT-kB1-LMODN as an effective anti-cancer cells drug

Increasing doses of LMODNs of SEQ ID NO. 40 and 41, as well as the control ODNs of SEQ ID NO. 42 and 43, were liposomaly introduced (Lipofectamine 2000, Invitrogen) to T98MG gliomas cancer cells. Forty-eight hours later, cell viability was tested by CellTiter-Blue assay (Promega®). Abbreviations: LMODN [LNA (locked nucleic acids), Modified ODN (oligonucleotide)], mLMODN (mutated LMODN), Sur. (survival).

FIG. 11: The promoter region of MGMT carries binding site for NF-κB

Figure discloses the nucleic acid sequence of the MGMT promoter region (as also denoted by SEQ ID NO. 39 and GenBank Accession No. X61657), from location (−954) to (+204). The NF-κB binding sites are indicated (enlarged bold) and marked therein K1 (also denoted by SEQ ID NO. 17), K2 (also denoted by SEQ ID NO. 19), K3 (also denoted by SEQ ID NO. 21), K4 (also denoted by SEQ ID NO. 23) and K5 (also denoted by SEQ ID NO. 25). Transcription start site is indicated in arrow.

DETAILED DESCRIPTION OF THE INVENTION

MGMT is the only gene known to be critical to direct reversal repair of the biological effects of (O)6-methylguanine on DNA. The present invention clearly demonstrates that NF-κB plays a major role in the regulation of MGMT, a function not recognized before. It is known that NF-κB is activated as part of the DNA damage response. The role of Rel/NF-κB factors in the signaling cascade that is initiated with double stranded DNA breaks has become more clear in the last few years [Wu, Z H. et al. Science 311:1141-6 (2006)].

It was recently demonstrated that in response to (O)6-alkylating agents, tumor necrosis factor alpha-induced protein 3 is involved in a putative cytoplasmic signaling cascade which mediates NF-κB activation [Bredel, M. et al. J. Clin. Oncol. 24:274-87 (2006)], however the NF-κB-mediated pathway in response to stimuli induced by alkylating agents remains largely obscure.

Transient expression experiments disclosed by the present invention, suggest that the NF-κB/p65 homodimer is a significant factor involved in MGMT regulation, as transfection of p65 into HEK293 resulted in a 55-fold increase in the induction of MGMT expression, compared with eightfold increase in induction while using AP-1/c-Jun. Co-transfection of p65 with AP-1/c-Jun or p50 did not exert a synergistic effect on p65-derived MGMT expression (FIG. 2A, 2B). The indication that the p65 homodimer is the main player in NF-κB-induced MGMT expression is also supported by EMSA analysis, showing that two NF-κB binding sequences within the MGMT promoter can bind a complex of similar size to the complex that binds to the canonical NF-κB site. Furthermore, the addition of monoclonal antibodies against the active form of p65 to the probe-extract mixture resulted in a complete "supershift". The EMSA results imply that the NF-κB binding site located in position (−90) of the MGMT promoter (designated as NF-κB2 site, also denoted by SEQ ID NO. 2), which overlaps a Sp1 site, probably binds both NF-κB and Sp1 (FIG. 1C). Therefore, the relationship between NF-κB and Sp1 might affect MGMT induction. However, additional studies are required to determine whether the p65 homodimer alone is sufficient to regulate MGMT expression or whether its association with other factors, such as Sp1, AP-1 or additional Rel/NF-κB proteins is of importance.

MGMT promoter methylation has been associated with prolonged survival in patients with various cancers, especially malignant gliomas [Hegi, M E. et al. N. Engl. J. Med. 352:997-1003 (2005);]. A recent study analyzed time to tumor progression in relation to MGMT promoter methylation in patients with glioblastoma moltiforme and found significantly improved results in patients with methylated MGMT promoter [Hegi, (2005) ibid.]. It is conceivable that methylated regions of the MGMT promoter are located in closed nucleosome structures [Watts, G S. et al. Mol. Cell. Biol. 17:5612-9 (1997)], impeding transcription factor access to the promoter [Patel, S A. et al. Mol. Cell. Biol. 17:5813-22 (1997)]. DNA methylation may affect transcription through this mechanism. However, the inventors found that transient expression of p65 in HEK293 cells induces a 55-fold increase in MGMT mRNA (FIG. 2A), even though the cells bear a methylated MGMT promoter (FIG. 4A). A significant concordant relationship between the nuclear pattern of activated NF-κB/p65 molecules and MGMT expression in human oligodendrogliomas (FIG. 3A, 3B), was also demonstrated by the present invention. However, in these tumors there was no correlation between the methylation status of the MGMT promoter and MGMT expression (FIG. 4B). This was confirmed also in the glioma cell lines (FIG. 3C, 3D, 4A), indicating that MGMT promoter methylation is not an overruling factor in relation to MGMT expression.

The findings of the present invention imply that tumors displaying high constitutive NF-κB activity [Amit, S. et al. Semin. Cancer Biol. 13:15-28 (2003)] should also exhibit high MGMT expression. Furthermore, the NF-κB-derived MGMT expression should not be dependent on MGMT methylation status as demonstrated in the current study. This could account for conflicting observations on the correlation between MGMT promoter methylation and gene expression [Lin (2005) ibid.; Brell (2005) ibid.].

MGMT is over-expressed in many types of human tumors (for review, see [Margison, G P. et al. Carcinogenesis 24:625-35 (2003)]). The expression level can serve as a major predictor of chemosensitivity to alkylating agents such as temozolomide and BCNU [Hermisson, M. et al. J. Neurochem. 96:766-76 (2006); Pollack, I F. et al. J. Clin. Oncol. 24:3431-7 (2006)]. The present invention show that either high constitutive NF-κB activity (FIG. 5A) or ectopic p65 (FIG. 5B) stimulated significant cellular resistance to BCNU treatment, most probably through induction of MGMT expression. On the other hand, inhibition of NF-κB activity by the dominant ΔNI-κB sensitized the cells to BCNU (FIG. 5B).

It was previously shown that NF-κB is activated in response to alkylating agents and that high NF-κB activation is associated with chemoresistance [Weaver (2003) ibid.]. The results disclosed by the present invention suggest that MGMT is most likely the major player in NF-κB induced chemoresistance mediated by alkylating agents, as the inventors found that inhibition of MGMT activity by BG completely abrogated the p65-induced chemoresistance. Without being bound by the theory, the invention propose a model for a novel DNA damage repair molecular mechanism induced by NF-κB in response to exposure to alkylating agents. According to this simplified model (FIG. 6), cell exposure to alkylating agent (A), induces NF-κB activation (B), binding of NF-κB to its specific binding sites within the MGMT promoter (C), which is followed by augmented MGMT expression (D). MGMT then removes the alkyl/methyl adducts from the (O)6 atom of DNA guanine (E) and the guanine is restored (F).

In conclusion, the present invention provides the first evidence that MGMT is a target gene for NF-κB. It is possible that MGMT is only the first example of the role played by NF-κB in the regulation of DNA repair mechanisms. NF-κB involvement in DNA damage repair may include additional DNA repair genes. Isolation of the novel NF-κB specific binding sites within the MGMT promoter, as shown for the first time by the present invention, provides a powerful tool for using such sequences as competitors. Such competition eliminates NF-κB induced over-expression of MGMT, and thereby sensitizing cells to treatment with alkylating agents.

Thus, in a first aspect, the invention relates to isolated and purified nucleic acid sequence derived from the O(6)-Methylguanine-DNA-Methyltransferase (MGMT) promoter region. The nucleic acid sequence of the invention comprises at least one NF-κB binding site, and preferably, at least five NF-κB binding sites. These sites are comprised within a fragment of the MGMT promoter region.

It should be noted that the whole MGMT promoter region presented by GenBank Accession no. X61657 [gi:34556], is denoted by SEQ ID NO. 39, and also shown by FIG. 11. According to a specifically preferred embodiment, the nucleic acid sequence of the invention comprises the nucleic acid sequence of a fragment of the MGMT promoter, this fragment has the sequence as denoted by SEQ ID NO. 38, or any fragment, variant, derivative, homologue and mutant thereof.

As used herein, the term "nucleic acid" refers to polynucleotides such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded (such as sense or antisense) and double-stranded poly nucleotides. It should be noted that the term "isolated" as also used herein with respect to nucleic acids, such as DNA or RNA, refers to molecules separated from other DNAs, or RNAs, respectively, which are present in the natural source of the macromolecule.

A promoter is a regulatory region of DNA generally located upstream a gene and can have regulatory elements several kilobases away from the transcriptional start site (enhancers). Many eukaryotic promoters contain a TATA box (sequence TATAAA), which in turn binds a TATA binding protein which assists in the formation of the RNA polymerase transcriptional complex. The TATA box typically lies very close to the transcriptional start site (often within 50 bases). It should be particularly appreciated that the MGMT promoter does not contain TATA box, it rather contain CpG islend as the major of the house keeping genes.

According to one embodiment, the invention relates to a nucleic acid sequence comprising an NF-κB binding site derived from the MGMT promoter region. The sequence of the invention preferably comprises the nucleic acid sequence as denoted by any one of SEQ ID NO. 4, 5, 30, 32, 34, 28, 29, 31, 33 and 35 or any fragment, variant, derivative, homologue and mutant thereof. It should be noted that each of these sequences is a fragment of the nucleic acid sequence as denoted by SEQ ID NO. 38.

As clearly shown by the following Examples, the NF-κB binding site of the invention specifically binds to the p65 subunit of NF-κB. Thereby, binding of NF-κB to the specific site of the invention in the MGMT promoter region, results in enhanced expression of the MGMT gene leading to enhanced repair of DNA damage.

It should be appreciated that any of the NF-κB binding sites of the invention may comprise sequences derived from either the positive strand of the MGMT promoter region, or the negative strand. Therefore, according to a specifically preferred embodiment, the nucleic acid sequence of the invention may comprise a sequence derived from the positive strand of MGMT promoter region as denoted by any one of SEQ ID NO. 4, 5, 30, 32 and 34. In yet another specifically preferred embodiment, the nucleic acid sequence of the invention may comprise a sequence derived from the negative strand of MGMT promoter region as denoted by any one of SEQ ID NO. 28, 29, 31, 33 and 35, respectively, or any fragment, variant, derivative, homologue and mutant thereof. It should be appreciated that a DNA single strand is indicated herein as "sense" or "positive" strand, if an RNA version of the same sequence is translated or translatable into protein. A "negative strand" is its complementary "antisense" strand.

More particularly, the NF-κB binding site may comprise sequences derived from either the positive strand as denoted by SEQ ID NO. 4 or the negative strand as denoted by SEQ ID NO. 28. It should be noted that both sequences encompass nucleotide sequence located from nucleotide base at position −773 to nucleotide base at position −734 and comprise the NF-κB binding site which is also referred to as MGMT-κB1. It should be appreciated that the location of the nucleotide bases is referred to the transcription start site. According to another embodiment, the NF-κB binding site may comprise sequences derived from either the positive strand as denoted by SEQ ID NO. 5 or the negative strand as denoted by SEQ ID NO. 29. It should be noted that both sequences encompass nucleotide sequence located from nucleotide base at position −91 to nucleotide base at position −68 and comprise the NF-κB binding site which is also referred to as MGMT-κB2.

In yet another embodiment, the NF-κB binding site may comprise sequences derived from either the positive strand as denoted by SEQ ID NO. 30, or the negative strand as denoted by SEQ ID NO. 31. Both sequences encompass nucleotide sequence located from nucleotide base at position −876 to nucleotide base at position −918 and comprise the NF-κB binding site which is also referred to as MGMT-κB3. According to another particular embodiment, the NF-κB binding site may comprise sequences derived from either the positive strand as denoted by SEQ ID NO. 32, or the negative strand as denoted by SEQ ID NO. 33. These sequences encompass nucleotide sequence located from nucleotide base at position −311 to nucleotide base at position −339 and comprise the NF-κB binding site which is also referred to as MGMT-κB4. According to another embodiment, the NF-κB binding site may comprise sequences derived from either the positive strand as denoted by SEQ ID NO. 34, or the negative strand as denoted by SEQ ID NO. 35. It should be noted that both sequences encompass nucleotide sequence located from nucleotide base at position +105 to nucleotide base at position +74 and comprise the NF-κB binding site which is also referred to as MGMT-κB5.

According to one embodiment, preferred fragment of any of the nucleic acid sequences of the invention, may preferably comprises the nucleic acid sequence of the positive strand as denoted by any one of SEQ ID NO. 1, 2, 17, 19, 21, 23, 25, and the negative strand as denoted by any one of SEQ ID NO. 27, 18, 20, 22, 24 and 26.

A specifically preferred fragment of the nucleic acid sequence of the invention comprises a nucleic acid sequence as denoted by any one of SEQ ID NO. 1 and SEQ ID NO. 27, or any fragment, mutant, homologue variant or derivative thereof.

More particularly, the NF-κB binding site comprised within a fragment of the nucleic acid sequence of the invention may comprise sequences derived from either the positive strand as denoted by SEQ ID NO. 1, or the negative strand as denoted by SEQ ID NO. 27. It should be noted that both sequences encompass nucleotide sequence located from nucleotide base at position −766 to nucleotide base at position −752 and comprise the NF-κB binding site which is also referred to as MGMT-κB1.

According to a specifically preferred embodiment, the nucleic acid sequence of the invention comprises a nucleic acid sequence of any one of GTAAAGTCCC, of the positive strand as denoted by SEQ ID NO. 17 and GGGACTTTAC, of the negative strand, as denoted by SEQ ID NO. 18, or any mutant, homologue variant or derivative thereof. It should be noted that these sequences are fragments of the nucleic acid sequence of the positive strand as denoted by SEQ ID NO. 1, or the negative strand as denoted by SEQ ID NO. 27, respectively. It should be noted the MGMT-κB1, is a non-canonical NF-κB binding site.

The following Examples clearly demonstrate the binding of the p65 subunit of NF-κB to the MGMT-κB1 site as denoted by SEQ ID NO. 18, which is derived from the negative strand of MGMT promoter region. It should be further appreciated that the invention further encompasses the nucleic acid sequence as denote by SEQ ID NO. 17, which is derived from the positive strand of MGMT promoter region and is therefore complementary to the sequence as denoted by SEQ ID NO. 18.

According to a specifically preferred embodiment, a mutant of the MGMT-NF-κB binding sites (for example, either the MGMT-KB1 or MGMT-κB2), may carry mutation in at least one of any of the nucleotide bases comprised within said site. According to a specific embodiment, a mutated molecule may carry a mutation in the C bases, specifically a C to G mutation. Non limiting examples for such mutated sites may comprise the sequences as denoted by any one of SEQ ID NO. 6 or 7. As shown by the invention, point mutation in these particular bases abolished the recognition and binding of these mutated sites by NF-κB. Therefore, alternative mutations may include mutations in any of the nucleotide bases of the MGMT-NF-κB sites, except a mutation in at least one of these CC bases. It should be therefore noted that the nucleic acid sequence of the invention may comprise at least one mutation such as, point mutation, nonsense mutation, missense mutation, deletion, insertion, rearrangement, or any combination thereof.

A second aspect of the invention relates to a construct comprising at least one repeat of a nucleic acid sequence of an NF-κB binding site derived from the MGMT promoter region. The construct of the invention comprises a nucleic acid sequence as denoted by any one of SEQ ID NO. 38, 4, 5, 30, 32, 34, 28, 29, 31, 33 and 35 or any fragment, variant, derivative, homologue and mutant thereof. By "derivatives" is meant the "fragments", "variants", "analogs" or "derivatives" of said nucleic acid sequence. A "fragment" of a molecule, such as any of the nucleic acid sequences of the present invention, is meant to refer to any nucleotide subset of the molecule. A "variant" of such molecule is meant to refer to a naturally occurring molecule substantially similar to either the entire molecule or a fragment thereof. An "analog" of a molecule can be a homologous molecule from the same species or from different species. The nucleic acid sequence of an analog or derivative may differ from the original sequence, when at least one base pair is deleted, inserted or substituted.

According to a specifically preferred embodiment, the construct of the invention comprises any of the nucleic acid sequences described by the invention.

According to a particularly preferred embodiment, any of the constructs of the invention may further comprise operably linked reporter gene. As a non-limiting example, such reporter genes may be selected from the group consisting of luciferase, green fluorescent protein (GFP) or other fluorescent proteins, secreted alkaline phosphatase (SEAP) and β-galactosidase (β-gal).

It should be appreciated that the constructs of the invention may be comprised within an expression vector or an expression vehicle.

"Expression Vehicles", as used herein, encompass vectors such as plasmids, viruses, bacteriophage, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. Generally, the genetic control elements can include a prokaryotic promoter system or a eukaryotic promoter expression control system. Such system typically includes a transcriptional promoter, an optional operator to control the onset of transcription, transcription enhancers to elevate the level of RNA expression, a sequence that encodes a suitable ribosome binding site, RNA splice junctions, sequences that terminate transcription and translation and so forth. Expression vectors usually contain an origin of replication that allows the vector to replicate independently of the host cell.

Plasmids are the most commonly used form of vector but other forms of vectors which serves an equivalent function and which are, or become, known in the art are suitable for use herein. See, e.g., Pouwels et al. Cloning Vectors: a Laboratory Manual (1985 and supplements), Elsevier, N.Y.; and Rodriquez, et al. (eds.) Vectors: a Survey of Molecular Cloning Vectors and their Uses, Buttersworth, Boston, Mass. (1988), which are incorporated herein by reference.

The term "operably linked" is used herein for indicating that a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

It should be therefore appreciated that all the constructs disclosed herein are encompassed within the scope of the present invention.

It should be further appreciated that the invention further encompasses any host cell transfected or transformed with any of the constructs of the invention. "Cells", "host cells" or "recombinant host cells" are terms used interchangeably herein. It is understood that such terms refer not only to the particular subject cells but to the progeny or potential progeny of such a cell. Because certain modification may occur in succeeding generation due to either mutation or environmental influences, such progeny may not, in fact, be identical to the parent cell, but are still included within the scope of the term as used herein. "Host cell" as used herein refers to cells which can be recombinantly transformed with vectors constructed using recombinant DNA techniques. A drug resistance or other selectable marker is intended in part to facilitate the selection of the transformants. Additionally, the presence of a selectable marker, such as drug resistance marker may be of use in keeping contaminating microorganisms from multiplying in the culture medium. Such a pure culture of the transformed host cell would be obtained by culturing the cells under conditions which require the induced phenotype for survival.

Still further, it should be recognized that the invention also encompasses any recombinant or fusion protein expressed by any of the host cells described by the invention.

The novel MGMT-NF-κB binding sites of the invention provide a powerful tool for controlling the expression of genes harboring said sequence in their regulatory regions. More particularly, these sites enable modulation of the expression of DNA repair enzymes, specifically, MGMT. One possible way of interfering with the NF-κB activity mediated by the elements of the invention, is to use oligonucleotides (ODNs) comprising the nucleic acid sequences of these NF-κB binding sites as competitors of the endogenous sequence within the MGMT promoter, for binding to NF-κB. It should be noted that experiments using "cold" (un-labeled) probes as shown in FIG. 1 of the specification demonstrate the feasibility of such strategy. cis DNA elements (decoys) are short double stranded DNA oligonucleotides, able to bind their target DNA binding proteins. The decoys according to the present invention are replicas of MGMT-NF-κB binding sites. Like the natural elements, the decoys are able to bind NF-κB. Therefore, when these elements are in surplus they will decoy NF-κB away from natural genomic elements. When regulatory factors, NF-κB in particular, are prevented from binding their target sequences, their regulatory effects on gene expression are generally impeded. The decoy strategy aims at providing an intracellular surplus of artificial DNA-binding sites for NF-κB, thus sequestering this factor from its natural site(s). In this way, transcription enhancement from the natural sites is prevented.

Thus, a third aspect of the invention relates to an NF-κB decoy in the form of an oligonucleotide (ODN) or oligonucleotide analogue comprising at least one repeat of at least one nucleic acid sequence of an NF-κB binding site derived from the MGMT promoter region. According to a preferred embodiment, the decoy molecule of the invention may comprise at least one repeat of at least one of any of the nucleic acid sequence as denoted by any one of SEQ ID NO. 4, 5, 30, 32, 34, 28, 29, 31, 33 and 35 or any fragment, variant, derivative, homologue and mutant thereof.

According to one embodiment, the ODN or ODN analogue of the invention may comprises at least one repeat of at least one of any of the nucleic acid sequences of the invention.

According to a specifically preferred embodiment, the decoy ODN or ODN analogue molecule of the invention comprises at least one repeat of a nucleic acid sequence of at least one of GTAAAGTCCC, as denoted by SEQ ID NO. 17 and GGGACTTTAC, as denoted by SEQ ID NO. 18, or any mutant, homologue variant or derivative thereof.

According to one preferred embodiment, the decoy molecules of the invention are short, preferably, double stranded DNA modified ODNs, able to bind their target DNA binding NF-κB protein, preferably the p65 subunit of NF-κB. According to one specifically preferred embodiment, the decoy molecule of the invention comprises at least one repeat of the sequence GGGACTTTAC, also designated MGMT-κB1 site as denoted by SEQ ID NO. 18, as well as of its complementary sequence GTAAAGTCCC, as denoted by SEQ ID NO. 17.

According to a specific and most preferred embodiment, a decoy molecule of the invention may comprise a double stranded modified ODN comprising the following MGMT-kB1 forward sequence:
5'-+T+Aagaggg+Actttacggg+Actttactac+A+T-3'   (also denoted by SEQ ID NO. 36). More specifically, the decoy molecule of the invention comprises a double stranded modified ODN comprising the following MGMT-kB1 reverse sequence:
5'-+A+Tgtagta+Agtcccgta+Aagtccctct+T+A-3 denoted by SEQ ID NO. 37).

In yet another specific and most preferred embodiment, a decoy molecule of the invention may comprise a double stranded modified ODN comprising the following MGMT-kB1 forward sequence:
5'---+T+Aatgggg+actttac ggg+Actttacaga+A+T---3' (as also denoted by SEQ. ID. NO. 40), with or without the 5' end labeled with carboxyfluorescein-5-succimidyl ester (FAM). More specifically, the decoy molecule of the invention comprises a double stranded modified ODN comprising the following MGMT-kB1 reverse sequence: 5'---+A+Ttctgta+Aagtcccgta+Aagtccccat+T+A---3' as also denoted by SEQ ID NO. 41).

According to one embodiment, the decoy molecules of the invention may comprise 1, 2, 3, 4, 5, 6, 7, 8, 9, 10, 20, 30, 40, 50, 60, 70, 80 90 or 100 repeats of any of the MGMT-NF-κB binding sites of the invention, preferably of MGMT-κB1 site, as shown for example by the decoys of SEQ ID NO. 36, 37, 40 and 41.

It should be noted that any of the bases marked in capital letter and + (for example +A, +T), is a modified nucleotide base. It should be further noted that wherein indicated modified nucleotide base or modified ODN, is meant also nucleotide base analogue or ODN analogue, respectively.

According to another preferred embodiment, the oligonucleotide or oligonucleotide analogue comprised within the decoy of the invention may be selected from the group consisting of DNA, RNA, LNA, PNA, INA and mixtures thereof and hybrids thereof, as well as phosphorous atom modifications thereof.

When used in the present context, the terms "locked nucleic acid monomer", "locked nucleic acid residue", "LNA monomer" or "LNA residue" refer to a bicyclic nucleotide analogue. LNA monomers are described in inter alia WO 99/14226, WO 00/56746, WO 00/56748, WO 01/25248, WO 02/28875, WO 03/006475 and WO 03/095467. By INA is meant an intercalating nucleic acid in accordance with the teaching of WO 03/051901, WO 03/052132, WO 03/052133 and WO 03/052134 incorporated herein by reference. An INA is an oligonucleotide or oligonucleotide analogue comprising one or more intercalator pseudonucleotide (IPN) molecules. Peptide nucleic acid (PNA) is an artificially synthesized polymer similar to DNA or RNA and is used in biological research and medical treatments. PNA is not known to occur naturally.

DNA and RNA have a deoxyribose and ribose sugar backbone, respectively, whereas PNA's backbone is composed of repeating N-(2-aminoethyl)-glycine units linked by peptide bonds. The various purine and pyrimidine bases are linked to the backbone by methylene carbonyl bonds. PNAs are depicted like peptides, with the N-terminus at the first (left) position and the C-terminus at the right.

According to a specifically preferred embodiment, the decoy of the invention comprises a modified LNA ODN, as also indicated by the present invention as
LMODN, comprises the sequence according to any of the ODN's as denoted by SEQ ID NO. 36 and 37, and 40 and 41 or any mixtures or combinations thereof.

As shown by the following Examples 7 and 8, the use of the LMODN decoy molecules of the invention clearly resulted in reduction of MGMT expression (as well as reduction in expression of the reporter gene), and significantly enhanced sensitization of glioma cells to treatment with alkylating agents.

More specifically, the decoy molecules of the invention therefore may lead to reduction, suppression, inhibition, attenuation, elimination, repression or weakening of the expression of MGMT or of any other coding region attached to the MGMT-κB binding sites of the invention, in about 10-100%, as compared to control. More specifically, the invention encompasses reduction of about 10%, 20%, 30%, 40%, 50%, 60%, 70%, 80%, 90%, 95% or 100% of the expression of a coding sequence attached to the MGMT-κB binding sites of the invention, preferably, MGMT expression.

Reduction of MGMT expression leads to increase, elevation or enhancement, of the cells sensitivity to alkylating agents, and thereby reduces cell survival. More specifically, the invention encompasses enhancement of cell sensitization to alkylating agents in about 10-100%, as compared to control cells not treated with the decoy molecule of the invention. More specifically, the invention encompasses enhancement of about 10%, 20%, 30%, 40%, 50%, 60%, 70%, 80%, 90%, 95% or 100% of cell sensitivity to alkylating agents.

Thus, as shown by the invention, the decoy molecule of the invention causes reduction of about 10-100% of cell survival, as compared to control. More specifically, reduction of about 10%, 20%, 30%, 40%, 50%, 60%, 70%, 80%, 90%, 95% or 100% of cell survival upon treatment with an alkylating agent, in response to treatment with the decoy molecules of the invention, as compared to control. It should be appreciated that cell sensitization and survival are demonstrated and disclosed by the following Example 8.

Therefore, it should be noted that the invention encompasses the use of any of the decoy molecules of the invention and any compositions or modifications and derivatives thereof, for reducing MGMT expression in a subject in need thereof and thereby, enhancing the sensitivity of cells of said subject, to alkylating agents.

As shown by Example 9, administration of higher doses (4 nM) of the decoy ODN molecules of the invention to cancer cells resulted in significant reduction in cell survival. These results illustrate the feasibility of using the ODN decoy molecules of the invention as an anti-cancerous drug.

Therefore, according to another embodiment, the invention provides the use of any of the ODN decoy molecules of the invention for the treatment of immune-related disorders, particularly of cancer.

The present invention provides methods and compositions for treating "immune-related" disorders. It should be appreciated that wherein indicated "related", is meant "associated", "caused by", "linked to", "usually occurring together" and "believed to have an impact on".

According to a further aspect, the invention relates to a composition comprising as an active ingredient an effective amount of at least one NF-κB decoy in the form of an oligonucleotide (ODN) or oligonucleotide analogue comprising at least one repeat of a nucleic acid sequence of at least one NF-κB binding site derived from the MGMT promoter region. More specifically, the decoy molecule of the invention may comprise at least one repeat of the nucleic acid sequence as denoted by at least one of any one of SEQ ID NO. 4, 5, 30, 32, 34, 28, 29, 31, 33 and 35 or any fragment, variant, derivative, homologue and mutant thereof.

According to one specific embodiment, the composition of the invention may comprise any of the decoy molecules described and provided by the invention or any combination or mixtures thereof.

In a particular embodiment, the composition of the invention may comprise at least one decoy molecule as denoted by any one of SEQ ID NO. 36, 37, 40 and 41, or any combinations thereof.

According to another preferred embodiment, any of the compositions of the invention may be used for inhibiting the NF-κB mediated enhancement of MGMT expression.

It should be appreciated that the decoy of the invention or any compositions thereof may be applicable in inhibition of NF-κB mediated expression of MGMT as well as of any DNA-repair enzyme, for example, DNA-PK, Ku70, Ku80, and ERCC-1.

In another embodiment, the composition of the invention may be used for inhibiting the NF-κB mediated enhancement of MGMT expression in a subject in need thereof.

As used herein, inhibition of the expression MGMT or of any relevant coding sequence attached to the MGMT-NK-κB binding sites of the invention by the decoy molecules of the invention or compositions thereof include inhibition of about 10-100%, more specifically, of about 10%, 20%, 30%, 40%, 50%, 60%, 70%, 80%, 90% or 100% of the expression, as compared to a control.

As shown by the following Example 9, administration of higher doses (4 nM) of the decoy ODN molecules of the invention to cancer cells resulted in significant reduction in cell survival. These results illustrate the feasibility of using the ODN decoy molecules of the invention as an anti-cancerous drug. Therefore, a preferred embodiment, the composition of the invention may be used as a drug for the treatment of immune-related disorders, particularly of cancer. Without being bound by the theory, reduction of MGMT expression may lead to recruitment of the DNA damage machinery and cause cell death.

Thus, the invention further provides a method for the treatment of immune-related disorders. The method of the invention comprises the step of administering to a subject in need thereof, a therapeutically effective amount of any of the ODN decoy molecules of the invention or of any composition comprising the same.

It should be noted that reduction of MGMT expression leads to reduction in DNA repair in said cells. Therefore, the composition of the invention may lead to increased sensitivity of such cells (having impaired DNA repair), to treatment with therapeutic agents causing DNA damage. Still further, the composition of the invention may be particularly suitable for sensitizing cells of a subject suffering of an immune-related disorder, to any therapeutic agent, particularly, therapeutic agents leading to DNA damage.

It should be appreciated that sensitization of cells to therapeutic agents includes elevation or increase of about 10-100%, more specifically, of about 10%, 20%, 30%, 40%, 50%, 60%, 70%, 80%, 90% or 100% of sensitivity, as compared to a control.

According to a preferred embodiment, the composition of the invention may be specifically used for increasing the sensitivity of cells, preferably of chemo-resistant cancer cells to a therapeutic agent, causing DNA damage, for example, an alkylating agent. Non limiting examples of therapeutic alkylating agents include drugs like temozolomide, streptozotocin, procarbazine, 1,3-bis(2-chloroethyl)-1-nitrosourea (BCNU) and dacarbazine.

As indicted herein before, alkylating agents are the most widely used anticancer drugs. They represent a large class of DNA damaging compounds that include drugs like temozolomide, streptozotocin, procarbazine, 1,3-bis(2-chloroethyl)-1-nitrosourea (BCNU) and dacarbazine. Therefore, according to one specific embodiment, the term alkylating agents includes, but not limited to Mustards, such as Meclotretamine, Cyclophosphamide, Melphalan, Clorambucil, Isophosphamide and Busulfan, Nitrosureas such as MNU, Carmustine (BCNU), Lemustine (CCNU), Semustine (MeCCNU), Fotemustine and Streptozotocin. Another class includes Tetrazinesuch as Dacarbazine, Mitozolomide and Temozolomide. A further classes encompassed herein may be Aziridine such as Thiotepa, Mytomicine and Cisplatin and analogs. It should e further noted that the invention further encompasses Non-classical alkylating agents such as Procarbazine and Hexamethylmelamine.

According to another preferred embodiment the composition of the invention may be specifically suitable for the treatment of an immune related disorder in a subject in need thereof.

More specifically, an immune related disorder according to the invention may be a malignant proliferative disorder, an inflammatory disorder or an autoimmune disorder.

According to a specific embodiment, the malignant proliferative disorder may be any one of solid and non-solid tumor selected from the group consisting of glioma, carcinoma, sarcoma, melanoma, leukemia and lymphoma. More particularly, the malignant disorder may be brain tumors. Brain tumor as used herein may be any intracranial tumor created by abnormal and uncontrolled cell division, either in the brain itself (neurons, glial cells (astrocytes, oligodendrocytes, ependymal cells), lymphatic tissue, blood vessels), in the cranial nerves (myelin-producing Schwann cells), in the brain envelopes (meninges), skull, pituitary and pineal gland, or spread from cancers primarily located in other organs (metastatic tumors).

Tumors occurring in the brain include: astrocytoma, pilocytic astrocytoma, dysembryoplastic neuroepithelial tumor, oligodendrogliomas, ependymoma, glioblastoma multiforme, mixed gliomas, oligoastrocytomas, medulloblastoma, retinoblastoma, neuroblastoma, germinoma and teratoma. Most primary brain tumors originate from glia (gliomas) such as astrocytes (astrocytomas), oligodendrocytes (oligodendrogliomas), or ependymal cells (ependymoma). There are also mixed forms, with both an astrocytic and an oligodendroglial cell component. These are called mixed gliomas or oligoastrocytomas. Mixed glio-neuronal tumors (tumors displaying a neuronal, as well as a glial component, e.g. gangliogliomas, disembryoplastic neuroepithelial tumors) and tumors originating from neuronal cells (e.g. gangliocytoma, central gangliocytoma). Other varieties of primary brain tumors include: primitive neuroectodermal tumors (PNET, e.g. medulloblastoma, medulloepithelioma, neuroblastoma, retinoblastoma, ependymoblastoma), tumors of the pineal parenchyma (e.g. pineocytoma, pineoblastoma), ependymal cell tumors, choroid plexus tumors and neuroepithelial tumors of uncertain origin (e.g. gliomatosis cerebri, astroblastoma).

In yet another embodiment, the malignant disorder may be e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

According to another embodiment, the composition of the invention may be applicable for any immune-related disorder involving NF-κB, or which are associated to DNA damage. An immune-related disorder may be for example, an inflammatory disorder or an autoimmune disease, (for example, Arthritis, multiple sclerosis (MS), Type-1 diabetes, lupus, Graves disease and thyroiditis, IBD), graft rejection pathology and graft versus host disease, and disorders induced by supper antigens, such as toxic shock, septic shock and severe sepsis.

According to another specifically preferred embodiment, the composition of the invention may further comprise an additional therapeutic agent. It should be appreciated that this specific embodiment provides the basis of a combination therapy. In many instances, combination therapies employing two or more therapeutic compounds are required to adequately address the medical condition and/or physical effects secondary to the condition under treatment. The present invention therefore particularly relates to additive and synergistic combinations of the decoy molecule of the invention with an additional therapeutic agent, preferably, an agent causing DNA damage.

By synergic combination is meant that the effect of both the decoy molecule of the invention and the additional therapeutic agent is greater than the sum of the therapeutic effects of administration of any of these compounds separately, as a sole treatment.

Thus, the invention further provides a combined composition comprising the decoy molecule of the invention and an additional therapeutic agent. Such additional agent may be an agent causing DNA damage, such as an alkylating agents and irradiation. Non limiting examples of therapeutic alkylating agents include drugs like temozolomide, streptozotocin, procarbazine, 1,3-bis(2-chloroethyl)-1-nitrosourea (BCNU) and dacarbazine.

Therefore, according to one embodiment, the invention provides a composition comprising a combination of at least one of any one of the decoy molecules of the invention and any mixture thereof and an additional therapeutic agent.

The invention further provides therefore, a pharmaceutical unit dosage form comprising at least one NF-κB decoy in the form of an oligonucleotide (ODN) or oligonucleotide analogue comprising at least one repeat of a nucleic acid sequence of at least one NF-κB binding site derived from the MGMT promoter region. More specifically, the pharmaceutical unit dosage form may comprise at least one of any of the decoy ODN molecules of the invention, or any combination or mixtures thereof.

More particularly, since the present invention relates to the treatment of diseases and conditions with an optional combination of active ingredients which may be administered separately, the invention also relates to combining separate pharmaceutical compositions in kit form.

The kit of the invention is intended for achieving a therapeutic effect in a subject in need thereof. According to one embodiment, the kit includes at least two separate pharmaceutical compositions:

(a) at least one NF-κB decoy in the form of an oligonucleotide (ODN) or oligonucleotide analogue comprising at least one repeat of a nucleic acid sequence of at least one NF-κB binding site derived from the MGMT promoter region, as defined by the invention, or any combination or mixtures thereof and optionally, a pharmaceutically acceptable carrier or diluent in a first unit dosage form;

(b) at least one additional therapeutic agent, specifically, an agent inducing DNA damage, and a pharmaceutically acceptable carrier or diluent in a second unit dosage form; and (c) container means for containing the first and the second dosage forms.

The kit form is particularly advantageous when the separate components are preferably administered in different dosage forms (e.g., oral and parenteral), are administered at different dosage intervals, or when titration of the individual components of the combination is desired by the prescribing physician.

Achieving a therapeutic effect is meant for example, where the kit is intended for the treatment of proliferative disorders, the therapeutic effect may be for example slowing the progression of the cancerous condition.

It should be appreciated that both components of the kit, the decoy molecule of the invention in the first dosage form and the different therapeutic agents causing DNA damage, in the second dosage form may be administered simultaneously. Alternatively, said first compound or dosage form and said second compound or dosage form are administered sequentially in either order.

According to one embodiment, the kit of the invention is intended for the treatment of a subject suffering from an immune-related disorder.

It should be appreciated that any of the compositions, combined compositions and kits of the invention may generally comprise a buffering agent, an agent who adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

It should be further appreciated that the decoy molecules or any kits, or compositions thereof may comprise an additional carrier facilitating the administration and penetration thereof to the treated subject. Of particular interest are the liposomes or alternatively the biodegradable polymers or any other nano-particle as described herein after by Example 11. The compositions, decoys or combined compositions of the present invention are generally administered in the form of a pharmaceutical composition comprising the compounds of this invention together with a pharmaceutically acceptable carrier or diluent. Thus, the compositions used by this invention can be administered either individually in a kit or together in any conventional oral, parenteral or transdermal dosage form.

The method of administration will be determined by the attendant physician or other person skilled in the art after an evaluation of the subject's conditions and requirements.

All aqueous solutions should be especially suitable for intravenous, intramuscular, subcutaneous and intraperitoneal injection purposes. In this connection, the sterile aqueous media employed are all readily obtainable by standard techniques well-known to those skilled in the art Methods of preparing various pharmaceutical compositions with a certain amount of active ingredient are known, or will be apparent in light of this disclosure, to those skilled in this art.

The invention further provides methods for treating immune-related disorder using the kit of the invention. It should be appreciated that the combined compositions or kits of the present invention may be administered in the form of a pharmaceutical composition comprising both the decoy molecules of the invention and an additional therapeutic agent together with a pharmaceutically acceptable carrier or diluent. Thus, the decoy molecules and optionally an additional therapeutic agent used by this invention can be administered either individually in a kit or together in any conventional oral, parenteral or transdermal dosage form.

Still further, the invention provides a method for sensitizing cells resistant to a therapeutic agent which causes DNA damage. According to a specific embodiment, such cell may be cells of a subject suffering from an immune-related disorder. Specifically, such cells may be cancer cells. The method of the invention comprises the step of contacting the cell with an effective amount of at least one NF-κB decoy in the form of an oligonucleotide (ODN) or oligonucleotide analogue comprising at least one repeat of a nucleic acid sequence of at least one NF-κB binding site derived from the MGMT promoter region. Preferably, the method of the invention may use any of the decoy molecules defined herein, or any combination, mixtures or compositions thereof. Specifically preferred examples are the decoy molecules as denoted by the sequence of any one of SEQ ID NO. 36, 37, 40 and 41, and any compositions kits and combinations thereof.

In yet another embodiment, the invention provides a method for sensitizing cells resistant to a therapeutic agent which causes DNA damage, in a subject suffering of an immune-related disorder. According to this embodiment, the method of the invention comprises the step of contacting the cell with an effective amount of at least one decoy in the form of an oligonucleotide (ODN) or oligonucleotide analogue comprising at least one repeat of a nucleic acid sequence of at least one NF-κB binding site derived from the MGMT promoter region, as defined by the invention, or any combination, mixtures or compositions thereof.

Still further, the invention relates to a method of treatment of an immune related disorder in a subject in need thereof. The method of the invention comprises the step of administering to the treated subject a therapeutically effective amount of at least one NF-κB decoy in the form of an oligonucleotide (ODN) or oligonucleotide analogue comprising at least one repeat of a nucleic acid sequence of at least one NF-κB binding site derived from the MGMT promoter region, as defined by the invention, or any combination, mixtures or compositions thereof.

According to one preferred embodiment, the method of treating immune-related disorders as defined by the invention may further comprises the step of administering to the treated subject a therapeutically effective amount of an additional therapeutic agent.

More specifically, an immune related disorder according to the invention may be a malignant proliferative disorder, an inflammatory disorder or an autoimmune disorder.

According to a specifically preferred embodiment, the method of the invention is particularly intended for treating a malignant proliferative disorder, for example, solid and non-solid tumor such as glioma, carcinoma, sarcoma, melanoma, leukemia and lymphoma.

As used herein to describe the present invention, "proliferative disorder", "malignant proliferative disorder", "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the methods and compositions of the present invention may be used in the treatment of non-solid and solid tumors.

In yet another embodiment, the autoimmune disease may be any one of rheumatoid arthritis, diabetes, asthma, acute and chronic graft versus host disease, systemic lupus erythmatosus, scleroderma, multiple sclerosis, inflammatory bowel disease and immune mediated hepatitis.

By "patient" or "subject in need" it is meant any mammal who may be affected by the above-mentioned conditions, and to whom the treatment and diagnosis methods herein described is desired, including human, bovine, equine, canine, murine and feline subjects. Preferably said patient is a human. Administering of the drug combination to the patient includes both self-administration and administration to the patient by another person.

According to a preferred embodiment, the decoy molecules of the invention as well as any compositions and kits thereof may be used for supporting and enhancing the therapeutic effect of other known therapeutic agents, alkylating agents for example. Therefore, according to a specifically preferred embodiment, the method of the invention may comprises a further step of administering to the treated subject, an additional therapeutic agent, either prior, with or after the administration of the decoy molecules of the invention. It should be noted that administration of the decoy molecules of the invention prior to or with alkylating agents may enhance the therapeutic effect of these agents. Therefore, according to a preferred embodiment, the method of the invention comprises an additional step of administering a therapeutic alkylating agent either with or after the administration of the decoy molecules of the invention, preferably, after.

According to another specific embodiment, the active ingredients used by the invention or composition comprising the same or combination thereof, may be administered via any mode of administration. For example, oral, intravenous, intramuscular, subcutaneous, intraperitoneal, parenteral, transdermal, intravaginal, intranasal, mucosal, sublingual, topical, rectal or subcutaneous administration, or any combination thereof.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician.

Therapeutic formulations may be administered in any conventional dosage formulation. Formulations typically comprise at least one active ingredient, as defined above, together with one or more acceptable carriers thereof.

It should be appreciated that the invention further provides the use of a therapeutically effective amount of at least one NF-κB decoy of the invention or any combination and mixtures thereof in the preparation of a composition for the treatment of an immune-related disorder. More specifically, the decoy used by the invention may be in the form of an oligonucleotide (ODN) or oligonucleotide analogue comprising at least one repeat of a nucleic acid sequence of an NF-κB binding site derived from the MGMT promoter region, as defined by the invention.

The novel MGMT-NF-κB binding sites defined by the present invention enables the use of such regulatory elements, as a target molecule for searching novel molecules having inhibitory effect on NF-κB mediated enhanced expression of MGMT. Such inhibitory compounds may potentially affect DNA damage repair mechanisms involving MGMT and therefore may be used for sensitizing cells to therapeutic agents leading to DNA damage. This may be particularly applicable in treating immuno-related disorders, and specifically proliferative disorders. The present invention therefore provides a high throughput screening methods for compounds which increase chemo-sensitivity of cells to a therapeutic agent, through inhibition of NF-κB mediated expression of MGMT.

Thus, a further aspect of the invention relates to a screening method for a compound which inhibits NF-κB mediated expression of MGMT and thereby increase sensitivity to therapeutic agents, specifically agents causing DNA damage, in a subject in need thereof. According to one embodiment, the screening method of the invention comprises three main stages: (a) obtaining a candidate compound which binds a nucleic acid sequence comprising an NF-κB binding site derived from the MGMT promoter region, as defined by the invention, or any fragment, variant, derivative, homologue and mutant thereof; (b) selecting from the candidate compounds obtained in step (a), a compound which inhibits the expression of a reporter gene operably linked to a nucleic acid sequence comprising an NF-κB binding site derived from the MGMT promoter region, as defined by the invention; and (c) determining the effect of the compound selected in step (b), on MGMT expression. It should be noted that the reduction of NF-κB mediated expression of MGMT by the candidate compound is indicative of the potential ability of such compound to increase sensitivity of a subject in need thereof to therapeutic agents causing DNA damage.

According to one preferred embodiment, the first stage of screening method of the invention involves the identification of a compound which specifically binds to the MGMT derived NF-κB binding site of the invention. As indicated above, identification of such compound involves the use of the novel NF-κB binding sites of the invention as a target. Therefore, the candidate modulating compound may be obtained by the steps of:

(a) providing a mixture comprising a nucleic acid sequence of an NF-κB binding site derived from the MGMT promoter region, as defined by the invention, or any fragment, variant, derivative, homologue and mutant thereof;

(b) contacting said mixture with the candidate compound under suitable conditions for binding; and (c) determining the effect of the candidate compound on an end-point indication, whereby modulation of said end point is indicative of binding of said nucleic acid sequence to the candidate compound.

According to one embodiment, the end point indication may be the binding of the nucleic acid sequence of the invention (NF-κB binding site) to the candidate compound, which leads to a visually detectable signal.

It should be noted that preferably, the nucleic acid sequence of the invention, or any fragments thereof, particularly, the NF-κB binding site, may be labeled and binding may be determined using for example, gel retardation assay. Alternatively, the candidate compounds may be immobilized to a solid support (a plate or membrane for example), and binding of the labeled sequence may be detected by a suitable means (radioactive labeling, avidin-biotin, Enzymatic reaction leading to a visual signal). In yet another alternative, specifically where the candidate compound is a protein compound, binding may be examined using affinity chromatography, ELISA, Western blots South-Western etc.

According to another specifically preferred embodiment, the second stage of the screening method of the invention involves functional examination of the candidate compounds obtained. Therefore, this stage is based on the selection of a candidate compound which in addition to its binding to the NF-κB binding site of the invention, also and thereby inhibits the expression of a reporter gene operably linked thereto. According to a preferred embodiment, the selection may be performed by the steps of: (a) providing a mixture comprising a reporter gene operably linked to a nucleic acid sequence of an NF-κB binding site derived from the MGMT promoter region, as defined by the invention, or any fragment, variant, derivative, homologue and mutant thereof; (b) contacting such mixture with the tested candidate compound under suitable conditions for expression of the reporter gene; and (c) determining the effect of the candidate compound on an end-point indication, whereby modulation of such end point is indicative of the ability of said compound to inhibit gene expression of the reporter gene via said NF-κB binding site.

According to another specifically preferred embodiment, the third stage of the screening method of the invention involves further evaluation of the feasibility of the selected candidate compounds to actually inhibit NF-κB mediated expression of MGMT. In such approach, the ability of the candidate compound to increase sensitivity of cells to therapeutic agents causing DNA damage is further examined. Therefore, the selected candidate compounds are next evaluated for their ability to inhibit MGMT expression by the following steps: (a) providing a test system comprising a gene encoding MGMT or any fragments thereof; (b) contacting the test system with a candidate compound obtained and selected by the method of the invention, under conditions suitable for expression of said MGMT; and (c) determining the effect of the tested candidate compound on an end-point indication as compared to a control. Such effect may reflect the ability of the candidate compound to inhibit NF-κB mediated expression of MGMT.

It should be indicated that the test system used by the screening method of the invention may be either in-vitrolex-vivo cell culture or an in-vivo animal model.

It should be further appreciated that the test system used by the method of the invention may optionally further comprises endogenous and/or exogenous compounds which provide suitable conditions for MGMT expression and for the detection of an end-point indication for determining the chemo-sensitizing effect of the candidate compound. Molecules essential for regulation of MGMT expression mediated by the NF-κB binding site of the invention, may be for example, the p65 subunit of NF-κB or any other subunit of NF-κB.

It should be noted that inhibition of MGMT expression by the candidate compound is as compared to a suitable control.

A further evaluation of the compound identified by the screening method of the invention may involve determination of its ability to reduce cell survival. Another example for evaluation of the compound may involve determination of its ability to increase sensitization of cells to a therapeutic agent, as measured by the effect of the tested compound on cell survival.

According to a preferred embodiment, the candidate compound examined by the method of the invention may be protein based, nucleic acid based, carbohydrates based, lipid based, small molecule, natural organic based, synthetically derived organic based, inorganic based or peptidomimetics based compounds.

According to a specifically preferred embodiment, the candidate compound may be a product of small molecule libraries.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps. Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Cell Culture and Medium

Glioma cell lines U87MG, T98G, A172, RG2 and HEK293T (human embryonic kidney) cells were obtained from the American Type Culture Collection (ATCC). U87MG and T98G were cultured in minimum essential medium supplemented with 2 mM L-glutamine, 1.5 g/L sodium bicarbonate, Earle's BSS (Sigma, Rehovot, Israel), 0.1 mM nonessential amino acids, 1.0 mM sodium pyruvate and 10% fetal bovine serum (Biological Industries, Beit Haemek, Israel), A172, RG2 and HEK293 cells were cultured in DMEM supplemented with 4 mM L-glutamine, 1.5 g/L sodium bicarbonate, (Sigma) and 10% fetal bovine serum (Biological Industries). All cells were maintained in a humidified incubator at 37° C. in 5% $CO_2$.

Cell Transfection

Transient transfections were performed in 6-well plates, using the FuGene6 transfection reagent (Roche Diagnostics GmbH, Mannheim, Germany), according to the manufacturer's instructions. U87MG, T98G, and A172 cells were transfected with pNF-κB-Luc reporter Vector (Clontech, Palo Alto, Calif.), while RG2 and U87MG were transfected with MGMT-Luc [construct p-954/+24 mL [Biswas T. et al. Oncogene 18:525-32 (1999)] kindly provided by Sankar Mitra] (1 μg/well). CMVβ-galactosidase expression vector (CMVβ-gal-Clonthech) was included (0.1 μg/well) in each transfection to normalize transfection efficiency. HEK293 cells were transfected with CMVβgal alone or along with one or more of the following plasmids: CMVp65, CMVΔNIκB, CMVp50, CMVcJun. CMVp65 and CMVΔNIκB plasmids were kindly provided by Prof. Yinon. Ben-Neriah (The Hebrew University, Jerusalem, Israel), CMVp50 and CMVcJun were kindly provided by Dr. Danielle Melloul (Hadassah Hebrew University Medical Center, Jerusalem, Israel).

Gel Electrophoretic Mobility Shift Assay (SMSA)

Nuclear extracts were prepared from HeLa cells treated with 200 units/ml of TNFα for 15 min. Oligodeoxynucleotides spanning the NF-κB binding site within the MGMT promoter (also denoted by SEQ ID NO. 4 and 5), with or without a C-G mutation (also denoted by SEQ ID NO. 6 and 7) or the consensus NF-κB site from HIV LTR (SEQ ID NO. 3, also shown in FIG. 1B), were end-labeled by a fill-in reaction using the Klenow fragment of DNA polymerase (New England Biolabs, Beverly, Mass.). DNA binding reactions were performed by incubation on ice for 15 min of 10 μg of nuclear extracts with 0.3 ng of $^{32}P$-labeled synthetic double-stranded oligodeoxynucleotides in the presence of 10 mM Hepes, pH 7.9, 10% glycerol, 50 mM KCl, 5 mM $MgCl_2$, 5 mM dithiothreitol, 2 μg of poly (dI·dC), and 0.1% Nonidet P-40. Competitor oligonucleotides were incubated in 100- fold molar excess and preincubated in the reaction mixtures for 10 min before addition of the radiolabeled probe. For supershift experiments, 1 µl of p65 antibody (MAB16200, Chemicon International Inc., Temecula, Calif.) was added during the preincubation period.

Real Time PCR

Total RNA was prepared using a SV total RNA kit (Promega, Madison, Wis.). cDNA was prepared from 1 µg of total RNA, using MuLV reverse transcriptase (Applied Biosystems, Warrington, UK) and random hexamers according to the manufacturer's instructions for first-strand cDNA synthesis. The reaction mixture included 1 µl of cDNA, 300 nM concentrations of the appropriate forward and reverse primers (Syntteza, Jerusalem, Israel), and 7.5 µl of the master mix buffer containing nucleotides, Taq polymerase, and SYBR green (SYBR Green Master Mix; Applied Biosystems, Warrington, UK), in a total volume of 15 Gene amplification was carried out using the GeneAmp 7000 Sequence Detection System (Applied Biosystems). Amplification included one stage of 10 min at 95° C., followed by 40 cycles of a two-step loop: 20 s at 95° C. and 1 min at 60° C. The gene expression results were normalized to the 18S rRNA gene.

All experiments were repeated 3-5 times in triplicate and are presented as the mean±s.d. The following primers were used for real time PCR:

```
                        (also denoted by SEQ ID NO. 9)
    18S:    F-5'-GGCCCTGTAATTGGAA;

(also denoted by SEQ ID NO. 10)
            R-5'-CCCTCCAATGGATCCTCGTT;

(also denoted by SEQ ID NO. 11)
    MGMT:   F-5'-GCAATTAGCAGCCCTGGCA;

(also denoted by SEQ ID NO. 12)
            R-5'-CACTCTGTGGCACGGGAT.
```

Immunohistochemical Staining

Five µm thick sections were deparaffinized in xylene, hydrated, and incubated with 10 mM sodium citrate buffer, pH 6.5. They were then heated by microwave (500 watts) for 30 min. The sections were left in the heated buffer for 10 min at room temperature. After 5 min treatment with 3% hydrogen peroxide, they were blocked by incubation with 3% bovine serum albumin for 30 min, followed by a 1-hr incubation with mouse monoclonal antibodies against human MGMT (1:50 dilution; MAB16200, Chemicon International Inc., Temecula, Calif.), or mouse monoclonal antibodies against human p65 (1:50 dilution; MAB16200, Chemicon International Inc.) at 37° C. The sections were then treated with secondary antibody (biotinylated anti-mouse avidin-biotin complex) (ABC Elite Kit; Vector Laboratories, Burlingame, Calif.) for 30 min at room temperature, and finally with avidin-peroxidase complex for 20 min, and developed with diaminobenzidine substrate (Sigma) according to the manufacturer's instructions. The nuclei were counterstained with hematoxylin (Sigma). In the negative controls the primary antibody was omitted. The level of MGMT protein expression was defined semi-quantitatively according to the fraction of positive nuclear staining, and was scored as high (50-100% positive nuclear staining) or low (0-49% positive nuclear staining). The semi-quantitative evaluation was performed by a pathologist (Y.F.) who was blinded to all the patients' details.

BG and BCNU Treatment and the Crystal Violet Viability Test

Various glioma cell lines (A172, U87MG, and T98G) or HEK293 were transiently transfected with different plasmids as indicated above. For the BG-treated groups, BG (Benzyl Guanine, an MGMT inhibitor) was added to the cell medium 4-6 hrs after transfection at a final concentration of 80 µM and incubated with the cells for the duration of the experiment. At 24 hrs following transfection, the cells were exposed for 2 hrs to increasing concentrations of BCNU (as indicated), which is a β-chloro-nitrosourea compound used as an alkylating agent in chemotherapy. The cells were fixed 48 hrs later with 4% paraformaldehyde for 20 min at room temperature, and washed twice with PBS. A 400 µl volume of 0.5% crystal violet in $dH_2O$ was added and the cells were stained for 15 min on a vibrator at 300 rpm. The dye was aspirated, the wells rinsed with dH2O, and the plate was allowed to dry in the hood. For destaining, 400 µl of 10% acetic acid were added to each well and the cells were incubated for 15 min on a vibrator at 300 rpm. The optical density ($OD_{590}$) of the de-stained solution in each well was read and recorded.

Treatment with Alkylating Agents and the Decoy ODN Molecules of the Invention and Testing Cell Survival T98MG glioma cell line cells were treated with increasing doses of the decoy ODN's of the invention. Double stranded ODNs (30mers), corresponding to MGMT-κB1 binding site (as also denoted by SEQ. ID. NO. 1), and control ODNs were purchased from IDT. Each strand of ODN was thirty-mers and contained six LNA nucleotides. The following ODNs were used: MGMT-kB1forward: 5'---+T+AATGGGG+ACTTTAC GGG+ACTTTACAGA+A+T---3' (as also denoted by SEQ. ID. NO. 40) with or without the 5' end labeled with carboxyfluorescein-5-succimidyl ester (FAM). The MGMT-kB1 reverse ODN: 5'---+A+TTCTGTA+AAGTCCCGTA+AAGTCCCCAT+T+A---3' as also denoted by SEQ ID NO. 41). Control forward: 5'---+T+AG TGT CG+A CTT CAC TCT+ACT TGA CAG A+A+T---3' (as also denoted by SEQ ID NO. 42), control reverse: 5'---+A+TT CTG TC+A AGT AGA GTG+AAG TCG ACA C+T+A---3' as also denoted by SEQ ID NO. 43). It should be noted that (+designated as nucleotide containing an LNA modification).

The viability of the cells was tested 24-48 hrs later by CellTiter-Blue assay (Promega®). The assay was carried out according to the supplier's instructions. Briefly, the assay is based on the ability of living cells to convert a redox dye (resazurin) into a fluorescent end product (resorufin). Cell viability estimation is done by measuring the fluorescent intensity of resorufin (ex. 560 nm, em. 590 nm) using a fluorescent microplate reader.

Luciferase Assay

At 24 hrs following transfection, the cells were lysed for 15 min on ice with 200 µl of luciferase lysis buffer (Promega, Madison, Wis.). Luciferase assays were carried out using a Promega assay kit and a luminometer (EG&G Berthold, Bad Wildbad, Germany). The activity was normalized to β-galactosidase activity (Promega) and plotted as the mean±s.d. of triplicates from a representative experiment.

Analysis of the Methylation Status of the MGMT Promoter

Genomic DNA (500 ng) from each cell line was chemically modified with sodium bisulfite to convert unmethylated cytosine to uracil while leaving methylcytosine unaltered (EZ DNA methylation kit; Zymo Research, Orange, Calif.). A 2 µl volume of the converted DNA was subjected to methylation-specific PCR (MSP), using two primer sets designed for amplifying the methylated or unmethylated allele of the MGMT promotor. Primer sequences of MGMT:

Unmethylated reaction: F-5'-TTTGTGTTTTGATGTTTG-TAGGTTTTTGT-3'; (also denoted by SEQ ID NO. 13) R-5'-AACTCCACACTCTTCCAA AAACAAAACA-3' (also denoted by SEQ ID NO. 14); Methylated reaction: F-5'-TTTCGACGTTCGTAGGTTT TCGC-3' (also denoted by SEQ ID NO. 15); R-5'-GCACTCTTCCGAAAAC-GAAACG-3' (also denoted by SEQ ID NO. 16). PCR was performed under the following conditions: an initial melting step of 10 min at 95° C.; followed by 50 cycles of 20 sec at 95° C., 20 sec at 59° C. and 45 sec at 72° C.; and a final elongation step of 4 min at 72° in a Gene Amp 9700 thermocycler (Applied Biosystems) using AmpliTaq Gold DNA polymerase (Applied Biosystems). Amplified products were separated on a 3.5% Methaphore gel and visualized under UV illumination.

Preparation of Constructs

For the cloning of the MGMT-luc constructs the reporter vector p-TA-Luc (Clontech, Palo Alto, USA) was used. The plasmid contains TATA box motif upstream to a luciferase reporter gene. A double stranded DNA corresponding to four repeats of each sequence as indicated by FIG. 8A (also denoted by SEQ ID NO. 44, 45, 46 and 47), was synthesis by syntezza LTD and ligated upstream to the TATA box.

Statistical Analysis

The non-parametric Kruskal-Wallis ANOVA test was applied to examine the statistical differences between study groups subjected to quantitative RT-PCR analysis or to BCNU treatment. When significant results were obtained, multiple pairwise comparisons were carried out between pairs of groups, using the Mann-Whitney test, with the Bonferroni correction for the significance level.

Fisher's Exact Test was applied to test the association between NFκB activation and the MGMT expression level in glial tumors or between MGMT expression and MGMT promoter methylation as categorical variables.

All tests applied were two-tailed and a p-value of 5% or less was considered statistically significant.

Example 1

Detection of Two Putative NF-κB Binding Sites Within the MGMT Promoter

As was previously shown by others, inhibition of NF-κB sensitizes cancer cells to alkylating agents [Weaver, K D. et al. J. Neurooncol. 61:187-96 (2003)]. Considering the fact that MGMT is a critical DNA repair enzyme involved in $O^6$-alkylguanine-induced effects, the inventors hypothesized that NF-κB might play a role in MGMT regulation. Therefore, using two different software tools (TFSEARCH; Genomatix) for computer analysis of the promoter region of MGMT, two putative binding sites for NF-κB were detected. One site was found to be located at position (−766), and the other overlapping a Sp1 binding site at position (−90). These sites were designated MGMT-κB 1 (also denoted by SEQ ID NO. 1) and MGMT-KB 2 (also denoted by SEQ ID NO. 2), as also demonstrated by FIG. 1A.

Example 2

Interaction between NF-κB/P65 and the NF-κB-Sites within the MGMT Promoter

To explore whether the NF-κB sites found within the MGMT promoter actually bind NF-κB, the inventors next performed an EMSA analysis of nuclear extracts from HeLa cells treated with TNFα and with labeled DNA fragments spanning the region containing the NF-κB motif. As shown by FIG. 1C, this process generated a nuclear binding factor specific for these regions (FIG. 1C, lanes 5 and 9), of the same size as the complex attached to the consensus HIV-κB site as also denoted by SEQ ID NO. 3 (FIG. 1C, lane 2) as indicated by the black arrows. The binding was abolished when a C-to-G substitution was introduced into the NF-κB-binding motif (FIGS. 1B and 1C, lanes 8 and 12, also denoted by SEQ ID NO. 6 and 7, respectively), demonstrating the specific requirement for this motif. Binding specificity was confirmed by competition with cold HIV-κB oligonucleotide. Addition of monoclonal antibodies against the NF-κB/p65 resulted in a 'supershift' (FIG. 1C, lanes 6 and 10). This confirmed that p65 binds to both NF-κB putative sites. The upper band in lane 9 (FIG. 1C) is not the same size as the NF-κB complex attached to the canonical HIV-κB oligonucleotide (FIG. 1C, lane 2). It was neither shifted when incubated with NF-κB/p65 antibodies (lane 10), nor abolished in the presence of unlabeled HIV-κB probe (FIG. 1C, lane 11). Based on the finding that the MGMT-κB2 binding site overlaps the Sp1 site, the inventors speculate that this complex may further contain Sp1. This speculation is also supported by its size, which is the same as that of the complex attached to the Sp1 oligonucleotide (FIG. 1C, lane 1). These results clearly indicate that there is a specific and direct interaction between NF-κB/p65 and the two NF-κB sites located within the MGMT promoter.

Example 3

Induction of MGMT mRNA Expression and MGMT Promoter-Dependent Reporter Gene by NF-κB To determine whether NF-κB plays a functional role in MGMT transcription, a quantitative RT-PCR analysis was next performed. As shown by FIGS. 2A and 2B, the MGMT mRNA level was 55-fold higher in HEK293 cells transiently transfected with CMV-p65, vs. the level in cells transfected with the CMVβgal control. This elevation was almost completely abolished by the addition of the non-degradable I-κBα mutant protein (CMVΔNI-κB). Transfection with CMV-cJun increased MGMT by eightfold, an observation that has been documented before [Boldogh, I. et al. Cancer Res. 58:3950-6 (1998)] Co-transfection of CMV-p65 and CMV-AP-1/c-Jun did not result in augmented MGMT mRNA, whereas co-transfection of CMV-p65 and CMV-p50 reduced by 50% the activity driven by CMV-p65 alone (FIGS. 2A and 2B). Induction of MGMT RNA following transfection with CMV-p65; CMV-cJun; CMV-p65 and CMV-AP-1/c-Jun or CMV-p65 and CMV-p50 was significantly different as compared with that in cells transfected with CMVβgal (p<0.001). These results were further confirmed by using a luciferase reporter gene driven by an hMGMT promoter fragment containing the two NF-κB binding sites. As shown by FIG. 2C, transfection of CMV-p65 into $R^G$-2 and U87MG cell lines induced MGMT promoter-dependent luciferase activity by 6 and 24 respectively, while CMV-ΔNI-κB almost completely abolished the induction.

Example 4

Significant Correlation between NF-κB Activation and the MGMT Expression Level in Glial Tumors and Cell Lines A high MGMT expression level is associated with tumor resistance to alkylating agents. To test whether the extent of NF-κB activation in tumor cells correlates with the protein expression level of MGMT, the inventors next immuno-histochemically stained 29 human oligodendroglioma sections for both NF-κB and MGMT, as shown by FIG. 3A. To selectively detect the activated form of NF-κB, a monoclonal antibody that recognizes an epitope overlapping the nuclear localization signal of the p65 subunit was used. The results of the semi-quantitative assessment of the NF-κB and MGMT nuclear staining (FIG. 3B) revealed a significant correlation (Fisher's exact probability test; $p<0.0001$) between NF-κB activation and MGMT expression (FIG. 3A). To confirm these results, three glioma cell lines (U87MG, A172, and T98G) that show differential RNA expression of MGMT, were used. As shown by FIG. 3C, NF-κB basal activity in each cell line was evaluated by quantifying luciferase activity 24 hrs following transfection with the pNF-κB-Luc reporter vector. MGMT expression levels in the different cell lines were identified by real time RT PCR, and are presented by FIG. 3D, as fold-induction relative to that of human lymphocytes. There was a correlation between NF-κB activity, as shown by the luciferase assay, and MGMT mRNA expression level (FIGS. 3C and 3D).

Example 5

MGMT Expression Correlates with NF-κB Activation Regardless of the Methylation Status of MGMT Promoter The relationship between MGMT promoter hypermethylation and loss of MGMT expression is controversial ever since it was first reported by Esteller, et al. [Esteller, (2000) ibid; Lin, Z. et al. J. Cancer Res. Clin. Oncol. 131:364-70 (2005); Brell, M. et al. Clin. Cancer Res. 11:5167-74 (2005)]. To determine whether there is a correlation between NF-κB activation, MGMT expression, and MGMT promoter methylation, the methylation status of the MGMT promoter was analyzed by MSP assay. In contrast to the differential pattern of NF-κB activation and MGMT expression in the various cell lines (FIG. 3C, 3D), the MGMT promoter was uniformly methylated in the A172, U87MG, and T98G cell lines (FIG. 4A). This discrepancy was also found in human oligodendrogliomas. Assessment of the MGMT promoter status of 16 oligodendrogliomas out of the 29 used earlier did not reveal any correlation between NF-κB activation, MGMT expression, and the MGMT methylation status (Fisher's exact probability test; $p=1$) (FIG. 4B). Furthermore, forced over-expression of p65 in HEK293 increased the MGMT expression level by 55-fold (FIG. 2), despite the fact that the MGMT promoter is methylated in those cells (FIG. 4A).

Example 6

NF-κB Activation Induces Chemoresistance

As shown above, high constitutive activation of NF-κB or ectopic p65 significantly stimulated MGMT expression. To determine whether this also results in induction of cellular resistance to alkylating agents, the sensitivity of the three glioma cell lines to increasing quantities of BCNU (5-80 μg/ml), was next compared. Viability tests demonstrated that the glioma cell line T98G, which exhibits high NF-κB activation and high MGMT expression, was significantly ($p<0.001$) more resistant to toxic doses of BCNU than the other two cell lines (FIG. 5A). To investigate whether this effect would also be obtained following forced expression of p65, HEK293 cells were transfected with CMVβgal alone or along with CMV-p65 or with CMV-p65 and CMV-ΔNI-κB. The cells were treated 24 hrs following transfection with BCNU (20-80 μg/ml) for 2 hrs. Viability tests performed 48 hrs later showed that cells transfected with CMV-p65 had acquired chemoresistance as compared to cells transfected with CMVβgal alone (at BCNU concentrations of 40 and 80 μg/ml $p<0.001$). As clearly shown by FIG. 5B, addition of CMV-ΔNI-κB abrogated this resistance ($p>0.4$).

To test whether the chemoresistance acquired by p65 is associated with MGMT and not with other NF-κB target genes, MGMT was depleted from the HEK293 transfected cells by administration of BG (Benzyl Guanine, an MGMT inhibitor) at 4-6 hrs after cell transfection. The results show that, BG treatment augmented the cell sensitivity to BCNU (FIG. 5B) bringing the control cells and the p65 transfected cells to display the same sensitivity. Therefore, it can be assumed that MGMT depletion restored the cell sensitivity to BCNU (at BCNU concentrations of 40 and 80 μg/ml $p<0.001$) in the p65-induced resistant cells.

Example 7

Interference with NF-κB Binding to MGMT-NF-κB1 Site Using Modified ODNs, Significantly Reduces Reporter Gene Expression The results obtained by the present invention strongly suggest that NF-κB inhibitors may overcome the MGMT-induced chemo-resistance.

These results encouraged the inventors to further investigate the therapeutic prospective of these findings and to examine whether interference with the binding of NF-κB to MGMT promoter may lead to decrease in MGMT expression level and thereby sensitize chemoresistant cancer cells to alkylating agents.

To investigate whether interference with NF-κB binding to MGMT promoter would reduce MGMT expression, a number of prototypes of locked nucleic acids (LNA) modified oligonucleotides (ODNs), also indicated as (LMODN), corresponding to the specific sequence of the two NF-κB sites within MGMT promoter were next designed. The LNA modification was chosen because it enhances the "drug" properties as LNA exhibits unprecedented affinity and specificity towards DNA, low toxicity, and an increased metabolic stability.

To test the activity of these sites, several luciferase reporter genes bearing four copies of either intact or mutant sequence, of each of the two NF-κB sites (NF-κB1 and NF-κB2), were constructed as indicated in Experimental procedures. As shown by FIG. 7, Co-transfection of MGMT-κB1 reporter construct with NF-κB/p65 demonstrated a 150 fold elevation in luciferase expression, while treatment with its corresponding modified ODN (as denoted by SEQ ID NO. 36 and 37), decreased the luciferase activity in a dose-dependent manner. An inhibition of approximately 50% was observed using 100 nM ODN. Negative control using the CMVΔNIκB (ΔN)-Luc construct as well as positive control using the canonical HIV-κB-Luc reporter construct, confirmed validity of the data. As shown by the Figure, co-transfection of MGMT-κB2 with NF-κB/p65, showed no expression of the reporter gene. These results clearly indicate that MGMT-kB1 may be the major binding site associated with MGMT induction.

Another example of interference of NF-κB induced exogenous expression of MGMT by the decoy ODN of the invention is demonstrated by FIG. 8. Induction of over expression of NF-κB in HEK 293T cells by transfection of a CMV-NF-κB/p65 generated a 50-fold elevation in luciferase expression driven by the Co-transfected reporter construct MGMT-kB1-Luc. Treatment of the cells, which underwent co-transfection with MGMT-kB1-Luc and NFκB/p65, with liposomal MGMT-kB1-ODN (as also denoted by SEQ ID NO. 40 and 41) inhibited the luciferase activity in a dose-dependent manner. Inhibition of approximately 90% was induced by 150 nM LMODN. The inhibitory activity of the LMODN (at 150 nM) was two fold greater than the inhibition obtained by the NF-κB super repressor, ΔNI-κB. No inhibition was detected when a mutant LMODN was introduced into the cells, indicating the specificity of MGMT-kB1-LMODN (of SEQ ID NO. 40 and 41). No inhibition was detected when a mutant ODN was introduced into the cells (data not shown), indicating that the MGMT-kB1-LMODN (of SEQ ID NO. 40 and 41) have a specific activity in inhibiting luciferase expression driven from the MGMT-κB 1 site within MGMT promoter. The MGMT-kB1-LMODN showed lower inhibitory activity (only 57% inhibition using 150 nm LMODN) on p65-induced luciferase expression once incited by a canonical NF-κB binding site from HIV of SEQ ID NO. 3 (HIV-κB-Luc construct). These results indicate that MGMT-kB1-LMODN is more specific for inhibition of MGMT than other NF-κB target genes.

To further confirm the binding of the NF-κB1 decoy LMODN molecules of the invention (as denoted by SEQ ID NO. 36 and 37), the ability of these modified ODN's to compete with the binding of p65 to MGMT-κB1, is tested by gel mobility shift assay using nuclear cell extract.

To test whether MGMT-kB1-LMODN can inhibit the expression of an endogenously expressed MGMT, the MGMT-kB1-LMODN decoy molecules of the invention are introduced into cancer cells that bear moderate or high MGMT expression, using commercially available liposomes (Lipofectamine 2000, Invitrogen). About twenty four to forty eight hours later, the level of MGMT RNA and protein expression is examined by RT real time PCR and Western blot analysis, respectively. For Western blot analysis, nuclear extracts are prepared as described for the EMSA analysis. Lysates containing 100 mg protein are separated by 12% SDS-PAGE and electroblotted onto Protran nitrocellulose transfer membrane (Schleicher & Schuell). Analysis is done using sequential probing with monoclonal antibody against MGMT (1:500 dilution; Chemiocon) and protein A-peroxidase (Amersham).

Example 8

MGMT-kB1-ODN Sensitizes Tumor Cells to Alkylating Agents

The inventors next tested the potential of the decoy LMODN molecules of the invention to sensitize tumor cells to alkylating agents and thereby improve their efficacy as anti-cancerous treatment. Therefore, several human cancer cell lines were treated with alkylating agents with increasing doses of MGMT-kB1-ODN followed by cell viability tests. First, the sensitivity of each cell line to several alkylating agents, mainly temozolomide (TMZ) and BCNU was calibrated. At 24 hrs following sowing, cells were exposed for two hours to increasing concentrations of the alkylating agent and viability of the cells was tested 24-48 hrs later by Cell-Titer-Blue assay (Promega®). To test the potential of MGMT-kB1-LMODN to sensitize tumor cells to alkylating agents in-vitro, increasing doses of LMODNs MGMT-kB1 forward and reverse as denoted by SEQ ID NO. 40 and 41, respectively), with or without the 5' end labeled with carboxyfluorescein-5-succimidyl ester (FAM), as well as the control LMODNs (as denoted by SEQ ID NO. 42 and 43), were liposomally introduced (Lipofectamine 2000, Invitrogen) to various tumor cancer cells. Twenty four hours later, cells were treated with the different doses of alkylating agents as calibrated before.

FIG. 9 represents an example of T98MG gliomas cell line sensitized to alkylating agents in response to treatment with the LMODN's of the invention. More particularly, cells were treated with 2.5 mM TMZ (temozolomide) with or without LMODN (see figure for concentrations and type of LMODN used). As clearly demonstrated by FIG. 9, treatment with 2 nm of MGMT-kB1-LMODN as denoted by SEQ ID NO. 40 and 41, sensitize the cells to TMZ and enhance cell mortality by approximately 300% (from 60% of live cells to only 22% of live cells). Furthermore, as shown by the viability of cells treated only with the LMODN, the decoy ODN used is not toxic to the cells. Moreover, the use of a mutant LMODN (mMGMT-kB1-LMODN, also indicated as the control ODNs, as denoted by SEQ ID NO. 42 and 43) that was also shown by FIG. 9 as having no any additive effect, indicates that the MGMT-kB1-LMODN activity shown is a specific activity.

Example 9

The MGMT-kB1-LMODN as a Single Drug Reduces Survival of Tumor Cells In-Vitro

Encouraged by the enhancing effect of the ODN molecules of the invention on treatment of cancer cells with alkylating agents, the inventors next examined the potential of these ODN molecules as single anti-cancerous drugs. Therefore, increasing doses of LMODNs were liposomally introduced (Lipofectamine 2000, Invitrogen) to various tumor cancer cells. Forty eight hours later, cell viability was tested, as indicated in Experimental procedures. FIG. 10 represents an example using T98MG gliomas cell line. As clearly shown by the Figure, treatment using 4 nM of MGMT-kB1-LMODN (also denoted by SEQ ID NO. 40 and 41) caused 80% cell mortality. In contrast, treatment of these cancerous cells with corresponding concentrations of the mutant LMODN (mMGMT-kB1-LMODN, as also denoted by SEQ ID NO. 42 and 43), showed no reduction in cell survival, indicating that the MGMT-kB1-LMODN has a specific activity. These results clearly demonstrate the feasibility of using the specific ODN molecules of the invention (MGMT-kB1-LMODN), as a single drug for reducing the survival of cancer cells. Without being bound by any theory, the inventors hypothesize that reduction of MGMT expression in response to treatment with the decoy molecules of the invention is sufficient to recruit DNA damage machinery leading to cell death.

In summary, the data presented by the invention clearly demonstrate specific and direct interaction of NF-κB with the MGMT promoter. The experiments disclose a substantial correlation between the extent of NF-κB activation and MGMT expression in glial tumors and exemplify that overexpression of NF-κB increases MGMT expression. Furthermore, the present invention shows that suppression of MGMT activity abolishes the chemoresistance acquired by NF-κB. These findings strongly suggest that MGMT is a major player in NF-κB-induced chemoresistance to alkylating agents. Still further, the invention shows that suppression of MGMT expression in tumor cells may be achieved if interference with the binding of NF-κB to MGMT promoter would be performed using the specific decoy LMODN molecules of the invention. This approach carries a potential major clinical significance as it may sensitize chemo-resistant, MGMT expressing cells, to alkylating chemotherapeutic treatment and it may also assist in overcoming treatment induced chemoresistance.

Example 10

In Vivo Evaluation of the Decoy LMODN Molecules of the Invention as Enhancing Chemotherapeutic Treatment Encouraged by the chemotherapeutic sensitivity enhancing effect of the decoy molecules of the invention, the inventor further evaluated the effect of these decoy molecules in vivo. Therefore, the safety and possible toxicity of the MGMT-kB1-ODN of the invention are next examined. For that purpose, the different LMODN decoy molecules of the invention are injected to mice at increasing doses, either alone or along with alkylating agents. Toxicity tests include examination of various organs such as the heart, liver, blood and brain.

Pharmacokinetics of the different MLODN decoy molecules is tested by labeling the ODNs with either FITC or p32, followed by tracing the labeled material in various organs and body fluids including serum, urine, liver and brain.

Example 11

Design of the LMODN Carrier

Screening the data bases for the suitable DNA carrier, for introducing the decoy molecules of the invention to a treated subject illuminated two kinds of carriers: The first are untargeted nanoparticles composed from biodegradable polymers, as poly (D,L lactide-co-glycolide) (PLGA) or stealth poly (Lactide-co-glycolide) monomethoxypoly (ethyleneglycol) (PLGAmPEG). The major advantage of these biodegradable nanoparticles is that their composition is relatively simple, and is considered to be non-toxic because they are composed from a biocompatible, degradable polymer. PLGA-DNA complexes have increased stability to degradation by DNase I, described as six times higher than naked DNA. Following an I.V. administration, PLGA nanoparticles yield 5-10 times higher plasma levels when compared to free drugs during the range of 4 hrs. Notably, dose increment decreased the rates of both blood clearance and mononuclear phagocyte system (MPS) uptake. It indicates a certain degree of MPS saturation at higher doses of PLGA nanoparticles. While, I.V. use of PLGA-mPEG nanoparticles followed a linear and dose-independent pharmacokinetic in addition to a prolonged blood residence. [Son, H J. Arch Pharm. Res. 30(8):1047-50 (2007); Takashima, Y. Int. J. Pharm. 1; 343(1-2):262-9 (2007)].

Another group of drug carrier belongs to immuno liposomes which are targeted liposome constructed with lipids and polyethylglycol (PEG), and an antibody attached to its steric barrier surface. For example, monoclonal antibodies (MAb) targeting the transferrin receptor, which is enriched at both the blood-brain barrier (BBB) and some peripheral tissues (liver, spleen). Persistent expression of the exogenous gene in brain, liver, and spleen was demonstrated for at least 6 days after a single intravenous injection of plasmid DNA packaged in pegylated immunoliposomes. [Shi, N. Pharm Res. 18:1091-5 (2001)].

The synthesis of the biodegradable nano-particles is performed by mixing together with the ODN molecules, thus, the biodegradable polymers spontaneously assemble with DNA to form nanoparticles. Synthetic biodegradable polymer which is non-toxic in vivo, such as polylactide (PLA), poly (lactide-co-glycolide) (PLGA), polyethyleneglycol (PEG), and polyalkylcyanoacrylate are considered. The constructed nanosphere is selected by the following desired parameters: small size; low profile of side effects and stable formulation between the drug and the drug delivery system (to prevent drug loss and ensure a stable delivery to the targeted organ or cell).

The synthesis of the pegylated immunoliposomes involves the use of a cationic or natural (uncharged) lipid coated with PEG, for example, PEG derivatives as $PEG^{2000}$. This derivative is bi-functional, it contains a maleimide at one end, for attachment to a thiolated MAb and a distearoylphosphatidylethanolamine (DSPE) moiety at the other end, for incorporation into the liposome surface. The targeted molecule is selected carefully to allow the receptor-mediated drug to penetrate the BBB. Transferrin receptor has been successfully used for delivery of other molecules across the BBB and therefore is considered among other targeted molecules.

The most efficient LMODN's are incorporated into the developed carrier and the resulting decoy is tested for in-vitro safety, cytotoxicity and efficacy of the incorporated drug carrier with the LMODN. Briefly, cells are exposed to increasing doses of the encapsulated-LMODN, and followed by alkylating agent treatment. For the cytotoxicity test the alkylating agent are omitted. Viability test is preformed as described in Example 8.

For testing safety and toxicity of the naked drug carrier in-vivo, the carrier is injected to mice at increasing doses, either alone or along with alkylating agents. The toxicity tests include evaluation of various organs such as the heart, liver, blood and brain.

Further evaluation of the in-vivo ability of the different decoy ODNs of the invention as a medicament increasing sensitization of cancer cells to alkylating chemotherapy is analyzed by establishment of an in-vivo tumor model and the calibration of the alkylating agent doses that are effective in reducing the size of the incited tumors. Nude or SCID mice with implanted tumors are therefore injected with various concentrations of alkylating agents and the size of the tumor is monitored by MRI.

In-vivo evaluation of toxicity and pharmacokinetics of the encapsulated LMODN is also examined. Once safe drug doses are determined and critical issued related to pharmacokinetics are known, pre-clinical in vivo efficacy trials are performed.

TABLE 1

Description of sequences in sequence listing

| SEQ ID NO. | DESCRIPTION |
| --- | --- |
| 1 | MGMT-kB 1(−766) to (−752) positive strand |
| 2 | MGMT-kB 2 (−90) to (−75) positive strand |
| 3 | Consensus HIVkB NF-κB site from HIV LTR |
| 4 | MGMT-kB 1 (−773 to −734) |
| 5 | MGMT-kB 2 (−91 to −68) |
| 6 | MGMT-kB 1 Mut |
| 7 | MGMT-kB 2 Mut |
| 8 | SP1 binding site |
| 9 | Real-Time PCR 18S F primer |
| 10 | Real-Time PCR 18S R primer |
| 11 | Real-Time PCR MGMT F primer |
| 12 | Real-Time PCR MGMT R-primer |
| 13 | Primer MGMT unmetylated F-primer |
| 14 | Primer MGMT unmetylated R-primer |
| 15 | Methylated reaction: F- primer |
| 16 | Methylated reaction: R- primer |
| 17 | MGMT-kB 1 site, positive strand |
| 18 | MGMT-kB 1site, negative strand |

TABLE 1-continued

Description of sequences in sequence listing

| SEQ ID NO. | DESCRIPTION |
|---|---|
| 19 | MGMT-kB 2 site, positive strand |
| 20 | MGMT-kB 2 site, negative strand |
| 21 | MGMT-kB 3 site, positive strand |
| 22 | MGMT-kB 3 site, negative strand |
| 23 | MGMT-kB 4 site, positive strand |
| 24 | MGMT-kB 4 site, negative strand |
| 25 | MGMT-kB 5 site, positive strand |
| 26 | MGMT-kB 5 site, negative strand |
| 27 | MGMT-kB 1(−752) to (−766), negative strand |
| 28 | MGMT-kB 1 (−734) to (−773), negative strand |
| 29 | MGMT-kB 2 (−68 to −91), negative strand |
| 30 | MGMT-kB 3 (−918 to −876), Positive strand |
| 31 | MGMT-kB 3 (−876 to −918), Negative strand |
| 32 | MGMT-kB 4 (−339 to −311), Positive strand |
| 33 | MGMT-kB 4 (−311 to −339), negative strand |
| 34 | MGMT-kB 5 (74 to 105), positive strand |
| 35 | MGMT-kB 5 (105 to 74), negative strand |
| 36 | LNA modified ODN of NF-κB1 |
| 37 | LNA modified ODN of NF-κB1 |
| 38 | A fragment of MGMT promoter region comprising NF-κB binding sites (−894 to +97) |
| 39 | MGMT promoter region (positive strand) as also denoted by Accession no. X61657 [gi: 34556] |
| 40 | MGMT-kB1 forward ODN |
| 41 | The MGMT-kB1 reverse ODN |
| 42 | Control forward |
| 43 | Control reverse |
| 44 | MGMT-kB1-Luc |
| 45 | MGMT-kB1Mut-Luc |
| 46 | MGMT-kB2-Luc |
| 47 | MGMT-kB2Mut-Luc |

The invention claimed is:

1. An isolated nucleic acid sequence comprising an NF-κB binding site derived from the O(6)-Methylguanine-DNA-Methyltransferase (MGMT) promoter region, wherein said sequence has the nucleic acid sequence as set forth in any one of SEQ ID NO. 4, 5, 30, 32, 34, 28, 29, 31, 33 and 35.

2. The nucleic acid sequence according to claim 1, wherein the nucleic acid sequence comprises a fragment of said sequence, said fragment being selected from a nucleic acid sequence as set forth in any one of SEQ ID NO. 1, 2, 17, 19, 21, 23, 25, 27, 18, 20, 22, 24 and 26.

3. The nucleic acid sequence according to claim 2, wherein the fragment of said sequence is selected from a nucleic acid sequence as denoted by any one of the positive strand of SEQ ID NO. 1 and the negative strand of SEQ ID NO. 27.

4. The nucleic acid sequence according to claim 3, wherein the fragment of said sequence is a nucleic acid sequence of any one of the positive strand of the sequence GTAAAGTCCC, as denoted by SEQ ID NO. 17 and the negative strand of the sequence GGGACTTTAC, as denoted by SEQ ID NO. 18.

5. A construct comprising at least one repeat of a nucleic acid sequence of an NF-κB binding site derived from the MGMT promoter region, wherein said sequence is selected from the nucleic acid sequence as denoted by any one of SEQ ID NO. 4, 5, 30, 32, 34, 28, 29, 31, 33 and 35.

6. The construct according to claim 5, wherein said nucleic acid sequence is as defined in any one of claims 2 to 4.

7. An NF-κB decoy in the form of a double stranded oligonucleotide (ODN) or oligonucleotide analogue comprising at least one repeat of at least one nucleic acid sequence of an NF-κB binding site derived from the MGMT promoter region, wherein said sequence has the nucleic acid sequence as set forth in any one of SEQ ID NO. 4, 5, 30, 32, 34, 28, 29, 31, 33 and 35.

8. The decoy according to claim 7, wherein said double stranded ODN or ODN analogue comprises at least one repeat of a nucleic acid sequence selected from any one of SEQ ID NO. 1, 2, 17, 19, 21, 23, 25, 27, 18, 20, 22, 24 and 26.

9. The decoy according to claim 8, wherein said double stranded ODN or ODN analogue comprises at least one repeat of a nucleic acid sequence of at least one of GTAAAGTCCC, as denoted by SEQ ID NO. 17 and GGGACTTTAC, as denoted by SEQ ID NO. 18.

10. The decoy according to claim 7, wherein the double stranded oligonucleotide or oligonucleotide analogue is selected from the group consisting of DNA, RNA, LNA, PNA, INA and mixtures thereof and hybrids thereof, as well as phosphorous atom modifications thereof.

11. A composition comprising as an active ingredient an effective amount of at least one NF-κB decoy in the form of an oligonucleotide (ODN) or oligonucleotide analogue comprising at least one repeat of at least one nucleic acid sequence of an NF-κB binding site derived from the MGMT promoter region, wherein said sequence has the nucleic acid sequence as denoted by any one of SEQ ID NO. 4, 5, 30, 32, 34, 28, 29, 31, 33 and 35.

12. The composition according to claim 11, wherein said decoy is in the form of a double stranded oligonucleotide (ODN) or oligonucleotide analogue comprising at least one repeat of at least one nucleic acid sequence selected from any one of SEQ ID NO. 1, 2, 17, 19, 21, 23, 25, 27, 18, 20, 22, 24 and 26.

13. The composition according to claim 12, for inhibiting the NF-κB mediated enhancement of MGMT expression.

14. The composition according to claim 12, for inhibiting the NF-κB mediated enhancement of MGMT expression in a subject in need thereof, and thereby sensitizing cells of said subject to a therapeutic agent.

15. The composition according to claim 14, for the treatment of an immune related disorder in a subject in need thereof.

16. A pharmaceutical unit dosage form comprising at least one NF-κB decoy in the form of an oligonucleotide (ODN) or oligonucleotide analogue comprising at least one repeat of at least one nucleic acid sequence of an NF-κB binding site derived from the MGMT promoter region, as defined in claim 7, or any combination or mixtures thereof.

17. A kit for achieving a therapeutic effect in a subject in need thereof comprising:
(a) at least one NF-κB decoy in the form of an oligonucleotide (ODN) or oligonucleotide analogue comprising at least one repeat of at least one nucleic acid sequence of an NF-κB binding site derived from the MGMT promoter region, as defined in claim 8, or any combination or mixtures thereof and optionally, a pharmaceutically acceptable carrier or diluent in a first unit dosage form;
(b) at least one additional therapeutic agent and a pharmaceutically acceptable carrier or diluent in a second unit dosage form; and
(c) container means for containing said first and second dosage forms.

18. A method for sensitizing cancer cells resistant to a therapeutic agent causing DNA damage, comprising the step of contacting said cell with an effective amount of at least one NF-κB decoy in the form of an oligonucleotide (ODN) or oligonucleotide analogue comprising at least one repeat of at least one nucleic acid sequence of an NF-κB binding site derived from the MGMT promoter region, as defined in claim 7, or any combination, mixtures or compositions thereof.

19. A method for the treatment of a malignant proliferative disorder in a subject in need thereof, wherein said method comprises the step of administering to said subject a therapeutically effective amount of at least one NF-κB decoy in the form of an oligonucleotide (ODN) or oligonucleotide analogue comprising at least one repeat of at least one nucleic acid sequence of an NF-κB binding site derived from the MGMT promoter region, as defined claim 7, or any combination, mixtures or compositions thereof.

* * * * *

SEQUENCE LISTING

```
<160> NUMBER OF SEQ ID NOS: 47

<210> SEQ ID NO 1
<211> LENGTH: 14
<212> TYPE: DNA
<213> ORGANISM: Homo sapiens

<400> SEQUENCE: 1
tctgtaaagt cccc                                                       14

<210> SEQ ID NO 2
<211> LENGTH: 15
<212> TYPE: DNA
<213> ORGANISM: Homo sapiens

<400> SEQUENCE: 2
gcgggaacac cccgc                                                      15

<210> SEQ ID NO 3
<211> LENGTH: 24
<212> TYPE: DNA
<213> ORGANISM: Homo  sapiens

<400> SEQUENCE: 3
ggcttcagag gggactttcc gaga                                            24

<210> SEQ ID NO 4
<211> LENGTH: 40
<212> TYPE: DNA
<213> ORGANISM: Homo sapiens

<400> SEQUENCE: 4
tgatggcttc tgtaaagtcc ccatctccaa ataaggtcac                           40

<210> SEQ ID NO 5
<211> LENGTH: 24
<212> TYPE: DNA
<213> ORGANISM: Homo sapiens

<400> SEQUENCE: 5
ggcgggaaca ccccgccccg cccg                                            24
```

-continued

```
<210> SEQ ID NO 6
<211> LENGTH: 40
<212> TYPE: DNA
<213> ORGANISM: Homo sapiens

<400> SEQUENCE: 6
tgatggcttc tgtaaagtcg gcatctccaa ataaggtcac                              40

<210> SEQ ID NO 7
<211> LENGTH: 24
<212> TYPE: DNA
<213> ORGANISM: Homo sapiens

<400> SEQUENCE: 7
ggcgggaaca cggcgccccg cccg                                              24

<210> SEQ ID NO 8
<211> LENGTH: 16
<212> TYPE: DNA
<213> ORGANISM: Homo sapiens

<400> SEQUENCE: 8
ctaactccgc ccatct                                                       16

<210> SEQ ID NO 9
<211> LENGTH: 16
<212> TYPE: DNA
<213> ORGANISM: Homo sapiens

<400> SEQUENCE: 9
ggccctgtaa ttggaa                                                       16

<210> SEQ ID NO 10
<211> LENGTH: 20
<212> TYPE: DNA
<213> ORGANISM: Homo sapiens

<400> SEQUENCE: 10
ccctccaatg gatcctcgtt                                                   20

<210> SEQ ID NO 11
<211> LENGTH: 19
<212> TYPE: DNA
<213> ORGANISM: Homo sapiens

<400> SEQUENCE: 11
gcaattagca gccctggca                                                    19

<210> SEQ ID NO 12
<211> LENGTH: 18
<212> TYPE: DNA
<213> ORGANISM: Homo sapiens

<400> SEQUENCE: 12
cactctgtgg cacgggat                                                     18

<210> SEQ ID NO 13
<211> LENGTH: 29
<212> TYPE: DNA
<213> ORGANISM: Homo sapience

<400> SEQUENCE: 13
tttgtgtttt gatgtttgta ggttttttgt                                        29
```

```
<210> SEQ ID NO 14
<211> LENGTH: 28
<212> TYPE: DNA
<213> ORGANISM: Homo sapiens

<400> SEQUENCE: 14
aactccacac tcttccaaaa acaaaaca                                          28

<210> SEQ ID NO 15
<211> LENGTH: 23
<212> TYPE: DNA
<213> ORGANISM: Homo sapiens

<400> SEQUENCE: 15
tttcgacgtt cgtaggtttt cgc                                               23

<210> SEQ ID NO 16
<211> LENGTH: 22
<212> TYPE: DNA
<213> ORGANISM: Homo sapiens

<400> SEQUENCE: 16
gcactcttcc gaaaacgaaa cg                                                22

<210> SEQ ID NO 17
<211> LENGTH: 10
<212> TYPE: DNA
<213> ORGANISM: Homo sapiens

<400> SEQUENCE: 17
gtaaagtccc                                                              10

<210> SEQ ID NO 18
<211> LENGTH: 10
<212> TYPE: DNA
<213> ORGANISM: Homo sapiens

<400> SEQUENCE: 18
gggactttac                                                              10

<210> SEQ ID NO 19
<211> LENGTH: 10
<212> TYPE: DNA
<213> ORGANISM: Homo sapiens

<400> SEQUENCE: 19
gggaacaccc                                                              10

<210> SEQ ID NO 20
<211> LENGTH: 10
<212> TYPE: DNA
<213> ORGANISM: Homo sapiens

<400> SEQUENCE: 20
gggtgttccc                                                              10

<210> SEQ ID NO 21
<211> LENGTH: 10
<212> TYPE: DNA
<213> ORGANISM: Homo sapiens

<400> SEQUENCE: 21
gggtctgtcc                                                              10
```

-continued

```
<210> SEQ ID NO 22
<211> LENGTH: 10
<212> TYPE: DNA
<213> ORGANISM: Homo sapiens

<400> SEQUENCE: 22
ggacagaccc                                                              10

<210> SEQ ID NO 23
<211> LENGTH: 10
<212> TYPE: DNA
<213> ORGANISM: Homo sapiens

<400> SEQUENCE: 23
ggactatccc                                                              10

<210> SEQ ID NO 24
<211> LENGTH: 10
<212> TYPE: DNA
<213> ORGANISM: Homo sapiens

<400> SEQUENCE: 24
gggatagtcc                                                              10

<210> SEQ ID NO 25
<211> LENGTH: 10
<212> TYPE: DNA
<213> ORGANISM: Homo sapiens

<400> SEQUENCE: 25
gggacagccc                                                              10

<210> SEQ ID NO 26
<211> LENGTH: 10
<212> TYPE: DNA
<213> ORGANISM: Homo sapiens

<400> SEQUENCE: 26
gggctgtccc                                                              10

<210> SEQ ID NO 27
<211> LENGTH: 14
<212> TYPE: DNA
<213> ORGANISM: Homo sapiens

<400> SEQUENCE: 27
ggggacttta caga                                                         14

<210> SEQ ID NO 28
<211> LENGTH: 40
<212> TYPE: DNA
<213> ORGANISM: Homo sapiens

<400> SEQUENCE: 28
gtgaccttat ttggagatgg ggactttaca gaagccatca                             40

<210> SEQ ID NO 29
<211> LENGTH: 24
<212> TYPE: DNA
<213> ORGANISM: Homo sapiens

<400> SEQUENCE: 29 cgggcgggc ggggtgttcc cgcc                                               24
```

```
<210> SEQ ID NO 30
<211> LENGTH: 36
<212> TYPE: DNA
<213> ORGANISM: Homo sapiens

<400> SEQUENCE: 30
cgaaggctcc acccaagggt ctgtcctctt aggctt                         36

<210> SEQ ID NO 31
<211> LENGTH: 36
<212> TYPE: DNA
<213> ORGANISM: Homo sapiens

<400> SEQUENCE: 31
aagcctaagt ggacagaccc ttgggtggag ccttcg                         36

<210> SEQ ID NO 32
<211> LENGTH: 29
<212> TYPE: DNA
<213> ORGANISM: Homo sapiens

<400> SEQUENCE: 32
cacgcccgcg gactatccct gtgacagga                                 29

<210> SEQ ID NO 33
<211> LENGTH: 29
<212> TYPE: DNA
<213> ORGANISM: Homo sapiens

<400> SEQUENCE: 33
tcctgtcaca gggatagtcc gcgggcgtg                                 29

<210> SEQ ID NO 34
<211> LENGTH: 29
<212> TYPE: DNA
<213> ORGANISM: Homo sapiens

<400> SEQUENCE: 34
cggatagctg ggacagcccg cgcccctag                                 29

<210> SEQ ID NO 35
<211> LENGTH: 29
<212> TYPE: DNA
<213> ORGANISM: Homo sapiens

<400> SEQUENCE: 35
ctaggggcgc gggctgtccc agctatccg                                 29

<210> SEQ ID NO 36
<211> LENGTH: 30
<212> TYPE: DNA
<213> ORGANISM: Homo sapiens

<400> SEQUENCE: 36
taagagggac tttacgggac tttactacat                                30

<210> SEQ ID NO 37
<211> LENGTH: 29
<212> TYPE: DNA
<213> ORGANISM: Homo sapiens

<400> SEQUENCE: 37
atgtagtaag tcccgtaaag tccctctta                                 29
```

```
<210> SEQ ID NO 38
<211> LENGTH: 990
<212> TYPE: DNA
<213> ORGANISM: Homo sapiens

<400> SEQUENCE: 38
agggaagggt ctgtcctctt aggcttctgg tggcttgcag gtgcagccct ccaatcctcc      60
tccccaagcg gcctgctgcc tataaggaca cgagtcatac tggatgaggg gcccactaat     120
tgatggcttc tgtaaagtcc ccatctccaa ataaggtcac attgtgaggt actgggagtt     180
aggactccaa catagcttct ctggtggaca caattcaact cctaataacg tccacacaac     240
cccaagcagg gcctggcacc ctgtgtgctc tctggagagc ggctgagtca ggctctggca     300
gtgtctaggc catcggtgac tgcagcccct ggacggcatc gcccaccaca ggccctggag     360
gctgccccca cggccccctg acagggtctc tgctggtctg ggggtccctg actagggag      420 cggcccagg aggggagaga ctcgcgctcc ggctcagcg tagccgcccc gagcaggacc      480
gggattctca ctaagcgggc gccgtcctac gaccccgcg cgctttcagg accactcggg      540
cacgtggcag gtcgcttgca cgcccgcgga ctatccctgt gacaggaaaa ggtacgggcc     600
atttggcaaa ctaaggcaca gagcctcagg cggaagctgg gaaggcgccg cccggcttgt     660
accggccgaa gggccatccg ggtcaggcgc acagggcagc ggcgctgccg gaggaccagg     720
gccggcgtgc cggcgtccag cgaggatgcg cagactgcct caggcccggc gccgccgcac     780
tgggcatgcg ccgacccggt cgggcgggaa caccccgccc cgcccgggct ccgccccagc     840
tccgcccccg cgcgcccccgg ccccgcccccc gcgcgctctc ttgcttttct caggtcctcg     900
gctccgcccc gctctagacc ccgcccacg ccgccatccc cgtgccctc ggccccgccc      960 ccgcgccccg gatatgctgg gacagcccgc                                     990

<210> SEQ ID NO 39
<211> LENGTH: 1157
<212> TYPE: DNA
<213> ORGANISM: Homo sapiens

<400> SEQUENCE: 39
ggatcctgct ccctctgaag gctccaggga agagtgtcct ctgctccctc cgaaggctcc      60
agggaagggt ctgtcctctt aggcttctgg tggcttgcag gtgcagccct ccaatcctcc     120
tccccaagcg gcctgctgcc tataaggaca cgagtcatac tggatgaggg gcccactaat     180
tgatggcttc tgtaaagtcc ccatctccaa ataaggtcac attgtgaggt actgggagtt     240
aggactccaa catagcttct ctggtggaca caattcaact cctaataacg tccacacaac     300
cccaagcagg gcctggcacc ctgtgtgctc tctggagagc ggctgagtca ggctctggca     360
gtgtctaggc catcggtgac tgcagcccct ggacggcatc gcccaccaca ggccctggag     420
gctgccccca cggccccctg acagggtctc tgctggtctg ggggtccctg actagggag      480 cggcccagg aggggagaga ctcgcgctcc ggctcagcg tagccgcccc gagcaggacc      540
gggattctca ctaagcgggc gccgtcctac gaccccgcg cgctttcagg accactcggg      600
cacgtggcag gtcgcttgca cgcccgcgga ctatccctgt gacaggaaaa ggtacgggcc     660
atttggcaaa ctaaggcaca gagcctcagg cggaagctgg gaaggcgccg cccggcttgt     720
accggccgaa gggccatccg ggtcaggcgc acagggcagc ggcgctgccg gaggaccagg     780
gccggcgtgc cggcgtccag cgaggatgcg cagactgcct caggcccggc gccgccgcac     840
tgggcatgcg ccgacccggt cgggcgggaa caccccgccc cgcccgggct ccgccccagc     900
tccgcccccg cgcgcccccgg ccccgcccccc gcgcgctctc ttgcttttct caggtcctcg     960
```

```
gctccgcccc gctctagacc ccgcccacg ccgccatccc cgtgccctc ggccccgccc      1020 ccgcgccccg gatatgctgg gacagcccgc gcccctagaa cgctttgcgt cccgacgccc      1080
gcaggtcctc gcggtgcgca ccgtttgcga cttggtgagt gtctgggtcg cctcgctccc      1140
ggaagagtgc ggagctc                                                    1157
```

<210> SEQ ID NO 40
<211> LENGTH: 30
<212> TYPE: DNA
<213> ORGANISM: Homo sapiens

<400> SEQUENCE: 40

```
taatggggac tttacgggac tttacagaat                                        30
```

<210> SEQ ID NO 41
<211> LENGTH: 30
<212> TYPE: DNA
<213> ORGANISM: Homo sapiens

<400> SEQUENCE: 41

```
attctgtaaa gtcccgtaaa gtccccatta                                        30
```

<210> SEQ ID NO 42
<211> LENGTH: 30
<212> TYPE: DNA
<213> ORGANISM: Homo sapiens

<400> SEQUENCE: 42

```
tagtgtcgac ttcactctac ttgacagaat                                        30
```

<210> SEQ ID NO 43
<211> LENGTH: 30
<212> TYPE: DNA
<213> ORGANISM: Homo sapiens

<400> SEQUENCE: 43

```
attctgtcaa gtagagtgaa gtcgacacta                                        30
```

<210> SEQ ID NO 44
<211> LENGTH: 44
<212> TYPE: DNA
<213> ORGANISM: Homo sapiens

<400> SEQUENCE: 44

```
gtaaagtccc cgtaaagtcc ccgtaaagtc cccgtaaagt cccc                        44
```

<210> SEQ ID NO 45
<211> LENGTH: 44
<212> TYPE: DNA
<213> ORGANISM: Homo sapiens

<400> SEQUENCE: 45

```
gtaaagtcgg cgtaaagtcg gcgtaaagtc ggcgtaaagt cggc                        44
```

<210> SEQ ID NO 46
<211> LENGTH: 40
<212> TYPE: DNA
<213> ORGANISM: Homo sapiens

<400> SEQUENCE: 46

```
ggaacacccc ggaacacccc ggaacacccc ggaacacccc                             40
```

```
<210> SEQ ID NO 47
<211> LENGTH: 40
<212> TYPE: DNA
<213> ORGANISM: Homo sapiens

<400> SEQUENCE: 47
ggaacacggc ggaacacggc ggaacacggc ggaacacggc                              40
```